(12) United States Patent
Homma et al.

(10) Patent No.: US 8,837,863 B2
(45) Date of Patent: Sep. 16, 2014

(54) SIGNAL-PROCESSING DEVICE AND COMPUTER-READABLE RECORDING MEDIUM WITH SIGNAL-PROCESSING PROGRAM RECORDED THEREON

(71) Applicant: Tohoku University, Sendai (JP)

(72) Inventors: Noriyasu Homma, Sendai (JP); Yoshihiro Takai, Sendai (JP); Haruna Endo, Sendai (JP); Kei Ichiji, Sendai (JP); Masao Sakai, Sendai (JP); Makoto Yoshizawa, Sendai (JP)

(73) Assignee: Tohoku University, Sendai-shi (JP)

( * ) Notice: Subject to any disclaimer, the term of this patent is extended or adjusted under 35 U.S.C. 154(b) by 0 days.

(21) Appl. No.: 13/740,859

(22) Filed: Jan. 14, 2013

(65) Prior Publication Data
US 2013/0129255 A1 May 23, 2013

Related U.S. Application Data

(63) Continuation of application No. PCT/JP2011/066007, filed on Jul. 13, 2011.

(30) Foreign Application Priority Data

Jul. 14, 2010 (JP) ................................. 2010-160009

(51) Int. Cl.
*G06T 7/20* (2006.01)
*A61B 6/00* (2006.01)
*G06T 11/60* (2006.01)
*A61N 5/10* (2006.01)

(52) U.S. Cl.
CPC ................. *G06T 11/60* (2013.01); *A61B 6/542* (2013.01); *A61B 6/5258* (2013.01); *A61B 6/5217* (2013.01); *A61N 2005/1061* (2013.01); *A61B 6/487* (2013.01)
USPC ....................................................... 382/294

(58) Field of Classification Search
None
See application file for complete search history.

(56) References Cited

U.S. PATENT DOCUMENTS 6,757,423 B1 * 6/2004 Amini ........................... 382/154
7,555,151 B2 * 6/2009 Comaniciu et al. ........... 382/128
(Continued)

FOREIGN PATENT DOCUMENTS

JP 2006-051199 A 2/2006
JP 2007-105196 A 4/2007
(Continued)

OTHER PUBLICATIONS

Sarel and Irani "Separating Transparent Layers through Layer Information Exchange," 2004.*

(Continued)

*Primary Examiner* — Vu Le
*Assistant Examiner* — Alexander J Lesnick
(74) *Attorney, Agent, or Firm* — Westerman, Hattori, Daniels & Adrian, LLP

(57) ABSTRACT

A signal-processing device, which processes transparent images each expressed by transparent superimposition of a target such as an affected part and a background, includes a transparent image acquiring unit that acquires the transparent images each including the target at a plurality of times; a calculating unit that calculates a component of the transparent image originating from the target and a component of the transparent image originating from the background at a given time t among the plurality of times in association with estimated values of at least one of a distribution originating from the target and a distribution originating from the background and that evaluates consistency with the transparent images; and an updating unit that updates the estimated values of at least one of a distribution originating from the target and a distribution originating from the background at the time t based on the evaluation result.

16 Claims, 22 Drawing Sheets

(56) References Cited

U.S. PATENT DOCUMENTS

| | | | |
|---|---|---|---|
| 7,623,679 B2 * | 11/2009 | West et al. | 382/103 |
| 7,639,854 B2 * | 12/2009 | Schnarr et al. | 382/128 |
| 8,265,363 B2 * | 9/2012 | Orderud et al. | 382/128 |
| 2005/0074154 A1 * | 4/2005 | Georgescu et al. | 382/128 |
| 2005/0251029 A1 * | 11/2005 | Khamene et al. | 600/427 |
| 2006/0074292 A1 * | 4/2006 | Thomson et al. | 600/411 |
| 2007/0086639 A1 | 4/2007 | Sakaida | |
| 2007/0098239 A1 * | 5/2007 | Zhou et al. | 382/128 |
| 2007/0297566 A1 | 12/2007 | Urano et al. | |
| 2008/0039713 A1 | 2/2008 | Thomson et al. | |
| 2010/0027861 A1 * | 2/2010 | Shekhar et al. | 382/131 |
| 2010/0195881 A1 * | 8/2010 | Orderud et al. | 382/131 |
| 2010/0215234 A1 | 8/2010 | Yamada et al. | |
| 2011/0092793 A1 | 4/2011 | Thomson et al. | |

FOREIGN PATENT DOCUMENTS

| | | |
|---|---|---|
| JP | 2008-000190 A | 1/2008 |
| JP | 2008-000456 A | 1/2008 |
| JP | 2008-514352 A | 5/2008 |
| JP | 2010-194053 A | 9/2010 |
| JP | 2011-018269 A | 1/2011 |

OTHER PUBLICATIONS

Sarel and Irani "Separating Transparent Layers of Repetitive Dynamic Behaviors," 2005.*

International Search Report of PCT/JP2011/066007, mailing date of Aug. 23, 2011.

* cited by examiner

TRANSPARENT IMAGES BEFORE SEPARATION
(12 FRAMES APPROPRIATELY SELECTED FROM 110 FRAMES)

BACKGROUND PORTIONS AFTER SEPARATION
(12 FRAMES CORRESPONDING TO FIG. 14)

TRUE VALUE IMAGE OF TUMOR Ia AND BACKGROUND Ib

INITIAL IMAGE OF TUMOR Ia AND BACKGROUND Ib SEPARATED BY INITIAL IMAGE
IT CAN BE UNDERSTOOD THAT FALSE CONTOUR OF TUMOR REMAINS IN BACKGROUND Ib

ESTIMATED TUMOR IMAGE Ia AND BACKGROUND Ib SEPARATED BY ESTIMATED TUMOR IMAGE Ia
WHEN COMPARED WITH FIG. 17A, IT CAN BE UNDERSTOOD THAT HIGH ACCURACY SEPARATION IS REALIZED

BACKGROUND PORTIONS AFTER SEPARATION (1st TO 12th FRAMES)

SIGNAL-PROCESSING DEVICE AND COMPUTER-READABLE RECORDING MEDIUM WITH SIGNAL-PROCESSING PROGRAM RECORDED THEREON

CROSS-REFERENCE TO RELATED APPLICATIONS

This application is a continuation Application of a PCT international application No. PCT/JP2011/066007 filed on Jul. 13, 2011, and this application is based upon and claims the benefit of priority of the prior Japanese Patent Application No. 2010-160009, filed on Jul. 14, 2010 in Japan, the entire contents of which are incorporated by references.

FIELD

The present invention relates to a signal-processing device and a computer-readable recording medium with the signal-processing program recorded thereon.

BACKGROUND

For example, there are radiotherapy apparatuses that perform therapy by irradiating an affected part such as a tumor with a radiation ray, such as a proton ray, a heavy particle ray, or an X-ray.

When a radiotherapy apparatus irradiates an affected part with a radiation ray, the irradiation of the radiation ray is performed in consideration of a variation in the position or shape of the affected part due to the fact that the position or shape of the affected part is varied due to respiration or the like of a patient.

As an example of the radiation therapy, for example, methods (called pursuit irradiation) of irradiating an affected tissue with a radiation ray only when the affected tissue is moved to a predetermined irradiation position of the radiation ray have been put to practical use in order to irradiate the affected tissue with the radiation ray while suppressing the influence on a normal tissue of a patient. That is, in the pursuit irradiation, an affected part is intermittently irradiated with the radiation ray.

Further, methods (called tracking irradiation) of irradiating the irradiation position of a radiation ray while tracking the position of a moving affected part have been suggested. Furthermore, methods of irradiating a predicted position with a radiation ray by predicting a temporal variation (for example, a variation in the position of an affected part due to respiration of a patient) in the position of an affected part have been suggested.

For example, Patent Literature 1 discloses, for example, a method of acquiring transparent images for which subtle density differences are ensured by controlling irradiation timings for acquisition of the transparent images and activation timings for therapeutic radiation rays, a method of irradiating an affected part with the radiation ray with high accuracy and with reliability by predicting the most probable position of the affected part at the irradiation time of the therapeutic radiation ray based on time-series data, and a method of performing highly reliable irradiation control on an irradiation target by comparing the acquired transparent images of the irradiation target with a reference image for a specific evaluation factor.

Patent Literature 1: JP 2006-51199 A

SUMMARY

As a method of identifying (specifying) a variation in the position or shape of an affected part, there is a method of monitoring the position or shape of an affected part by performing X-ray photography on the vicinity of the affected part. Further, the X-ray photography is performed by, for example, an on board imager (OBI) that is mounted on a radiotherapy apparatus main body in a direction different from the irradiation direction of a therapeutic radiation ray, a kV-X-ray fluoroscope that is installed independently from a radiation therapy apparatus main body, and an MV-X-ray fluoroscope that uses a therapeutic radiation ray together.

However, in general, an image (a so-called transparent image) acquired through X-ray photography lacks in resolution or contrast, and the boundary between the tissue of an affected part and the peripheral tissue is not clear either, compared to a tomographic image acquired by a computed tomography (CT) or the like.

Therefore, in methods according to the related art, to easily identify the position of an affected part, a marker made of metal (for example, gold) is inserted in advance into the vicinity of the affected part and X-ray photography is performed on the vicinity of the affected part including the marker. Then, a variation in the position of the affected part is estimated by measuring the position of the metallic marker shown in transparent images acquired through the X-ray photography. This is because the transparent images of the metallic marker also have sufficient contrast.

However, when the metallic marker is inserted into the vicinity of the affected part, there is a risk of the health of a patient. For example, when an affected part is a lung tumor and a metallic marker is inserted into the vicinity of the lung tumor, lung emphysema, pneumothorax, or the like occurs in about 30% of a total of the patients.

Due to the risk, the insertion of a metallic marker into the vicinity of an affected part is not permitted in US and the like. Therefore, it is difficult to measure a variation in the position of an affected part. As a result, a sufficient therapy effect may not be expected due to deterioration in irradiation accuracy of a radiation ray to an affected part and a side-effect may occur due to erroneous irradiation to a normal tissue.

The invention is devised in view of the above-mentioned problems and an object of the invention is to measure (estimate) the position, shape, size, and the like of a target such as an affected part with high accuracy.

Another object of the invention is to measure (estimate) the position, shape, size, and the like of a target such as an affected part with high accuracy, with safeness, and with low burden without insertion of a metallic marker.

Still another object of the invention is to enable accurate irradiation to the affected part in radiation therapy.

The invention is not limited to the above-mentioned objects, but operational effects which are obtained from configurations described in embodiments to be described below and may not be obtained from the technologies according to the related art are obtained as another object of the invention.

(1) According to a first aspect of the invention, a signal-processing device or an image-processing device which processes transparent images each expressed by transparent superimposition of a target and a background different from the target may be used. The device includes a transparent image acquiring unit that acquires the transparent images each including the target at a plurality of times, a calculating unit that calculates a component of the transparent image originating from the target and a component of the transparent image originating from the background at a given time t among the plurality of times in association with estimated values of at least one of a distribution originating from the target and a distribution originating from the background at the plurality of times and that evaluates consistency with the transparent images at the plurality of times, and an updating unit that updates the estimated values of at least one of a distribution originating from the target and a distribution originating from the background at the time t based on the evaluation result of the calculating unit.

Here, the space dimension of the transparent image is not particularly limited, but may be one of one dimension, two dimensions, and three dimensions. The target (target portion) refers to a target to be detected in the transparent image or a portion corresponding to the target in a real space or the like corresponding to the transparent image. Further, the background (background portion) refers to a portion which is not included in the target. One target or two or more targets can be selected. When two or more targets are selected, the targets may be superimposed in the transparent image or may be present separately. There is no essential difference between the target and the background. One or a plurality of targets may be considered as backgrounds (that is, a plurality of backgrounds are considered to be present).

The transparent superimposition between the target and the background means that the target and the background are partially or entirely superimposed with each other with some weight. When the transparent superimposition is performed, the target and the background may not be separated from only the transparent image at the given time t. Accordingly, the calculating unit evaluates consistency between one or both of the component originating from the target and the component originating from the background at the given time t and the transparent images at the plurality of times (which may be the same as or may be different from the plurality of associated times) in association with estimated values of at least one of a distribution originating from the target and a distribution originating from the background at the plurality of times (which may include the time t). Here, the association can be formulated and calculated based on the characteristics (for example, which are recognized as physical characteristics, or statistical characters, or the like) of the transparent superimposition. Any range of the plurality of times associated with the time t may be set. However, when the target and the background (according to a use purpose) are considered to be separated with accuracy to some extent in a case in which the movements of the target and the background are temporally continuous, the plurality of times may be set in a temporal range (which is called the vicinity of the time t) in which a variation from the time t state can be regarded to be relatively small. For example, a way of using the transparent images at the time t and a time before or after the time adjacent to the time t can be considered. The evaluation of the consistency can be performed, for example, by quantitatively calculating the size of an appropriately defined error and comparing the size of the error with an appropriate value.

The updating unit updates the distribution so that the consistency is improved based on the evaluation result of the calculating unit, in other words, the adequacy of the separation is improved.

The distribution (distribution information) refers to information that indicates the distribution originating from the targets or the backgrounds in the transparent images. For example, the distribution can be expressed by spatial position information or luminance information or the like at each position. When the transparent image is digitized, for example, the position information may be set as existence information in each region (which may be formed by one pixel or a plurality of pixels) to be interested as a processing target, and the luminance information may be set as information regarding a representative luminance value of each area. When the position information is treated to be linear, for example, the position information can be expressed as coefficient matrix having coefficients regarding the pixel position of each region. Of course, the position information can be treated to be nonlinear. For example, when the target is expanded or contracted, the expression as a nonlinear function can be considered to be effective.

The target and the background may be separated through statistical analysis. For example, the adequacy of the separation can be evaluated by calculating existence or non-existence and the extent of the statistical independency of the target and the background for at least one component of the position, shape, and the luminance of the target and the background. An example of this analysis is independent component analysis.

(2) According to a second aspect of the invention, a signal-processing device or an image-processing device which processes transparent images expressed by transparent superimposition of L (where, L is a natural number) targets and a background other than the targets may be used. The device includes a transparent image acquiring unit that acquires the transparent image in regard to the target at a given time t, a measurement vector generating unit that takes an interest in M×N (where, M and N are natural numbers) regions in the transparent images acquired by the transparent image acquiring unit and generates a measurement vector b (t, $t_1$, $t_2$, ..., and $t_K$) (where, K is a natural number) corresponding to (K+1) times which consists of (K+1)×M×N luminance values in the regions of interest of the (K+1) transparent images acquired at the time t and K times $t_1$, $t_2$, ..., and $t_K$ prior to the time t, a variable vector updating unit that updates variable vectors (hereinafter, referred to as target variable vectors $I_{a1}$, $I_{a2}$, ..., and $I_{aL}$) consisting of at least one luminance value originating from the L targets in the region of interest, respectively and a variable vector (hereinafter, referred to as a background variable vector $I_b$) consisting of at least one luminance value of the background in the region of interest based on the measurement vector b, the background variable vector $I_b(t_p)$ and target variable vector $I_a(t_p)$ consisting of L variable vectors $I_{a1}(t_p)$, $I_{a2}(t_p)$, ..., and $I_{aL}(t_p)$ in regard to the region of interest of the transparent image at a time $t_p$ prior to the time t, and a variable vector calculating unit that calculates a variable vector I including the target variable vector $I_a$ and the background variable vector $I_b$ updated by the variable vector updating unit so that evaluation of an evaluation value PI defined by a function of the measurement vector b, the variable vector I, a coefficient matrix A of (K+1)MN×(L+1) MN regarding the positions of the L targets and the background at the time t estimated using the variable vector I and the estimated positions of the L targets and the background at the respective times being K previous times $t_1$, $t_2$, ..., and $t_x$:

$$PI=f(A,I,b) \qquad \text{[Expression 1]}$$

is increased, where f is a deterministic or stochastic function.

The acquisition of the transparent image by the transparent image acquiring unit, the generation of the measurement vector b by the measurement vector generating unit, the updating of the variable vector I by the variable vector updating unit, and the calculation of the variable vector I by the variable vector calculating unit are performed by shifting the time.

(3) According to a third aspect of the invention, a signal-processing program, which causes a computer that processes transparent images each expressed by transparent superimposition of a target and a background different from the target to realize the following functions, may be used: a transparent image acquiring function of acquiring the transparent images each including the target at a plurality of times; a calculating function of calculating a component of the transparent image originating from the target and a component of the transparent image originating from the background at a given time t among the plurality of times in association with estimated values of at least one of a distribution originating from the target and a distribution originating from the background at the plurality of times and that evaluates consistency with the transparent images at the plurality of times, and an updating function of updating the estimated values of at least one of a distribution originating from the target and a distribution originating from the background at the time t based on the evaluation result by the calculating function.

(4) According to a fourth aspect of the invention, a computer-readable recording medium that records the program may be used.

(5) According to a fifth aspect of the invention, a signal processing method including performing each of the above-described processes may be used.

Advantageous Effects of Invention

According to the invention, it is possible to measure (estimate) the position, shape, size, and the like of a target such as an affected part with high accuracy.

Further, it is possible to measure (estimate) the position, shape, size, and the like of a target such as an affected part with high accuracy, with safeness, and with low burden without insertion of a metallic marker.

Furthermore, it is possible to enable accurate irradiation to the affected part in radiation therapy.

DESCRIPTION OF EMBODIMENTS

Hereinafter, embodiments of the invention will be described with reference to the drawings. However, the embodiments to be described below are merely examples and various modifications or applications of the technology not described in the embodiments are not attempted to be excluded. That is, the embodiments can be modified (for example, the embodiments are combined) in various forms within the scope of the invention without departing from the gist of the invention.

[1] Embodiment (1.1) Example of Configuration of Radiotherapy Apparatus

Figure 1:
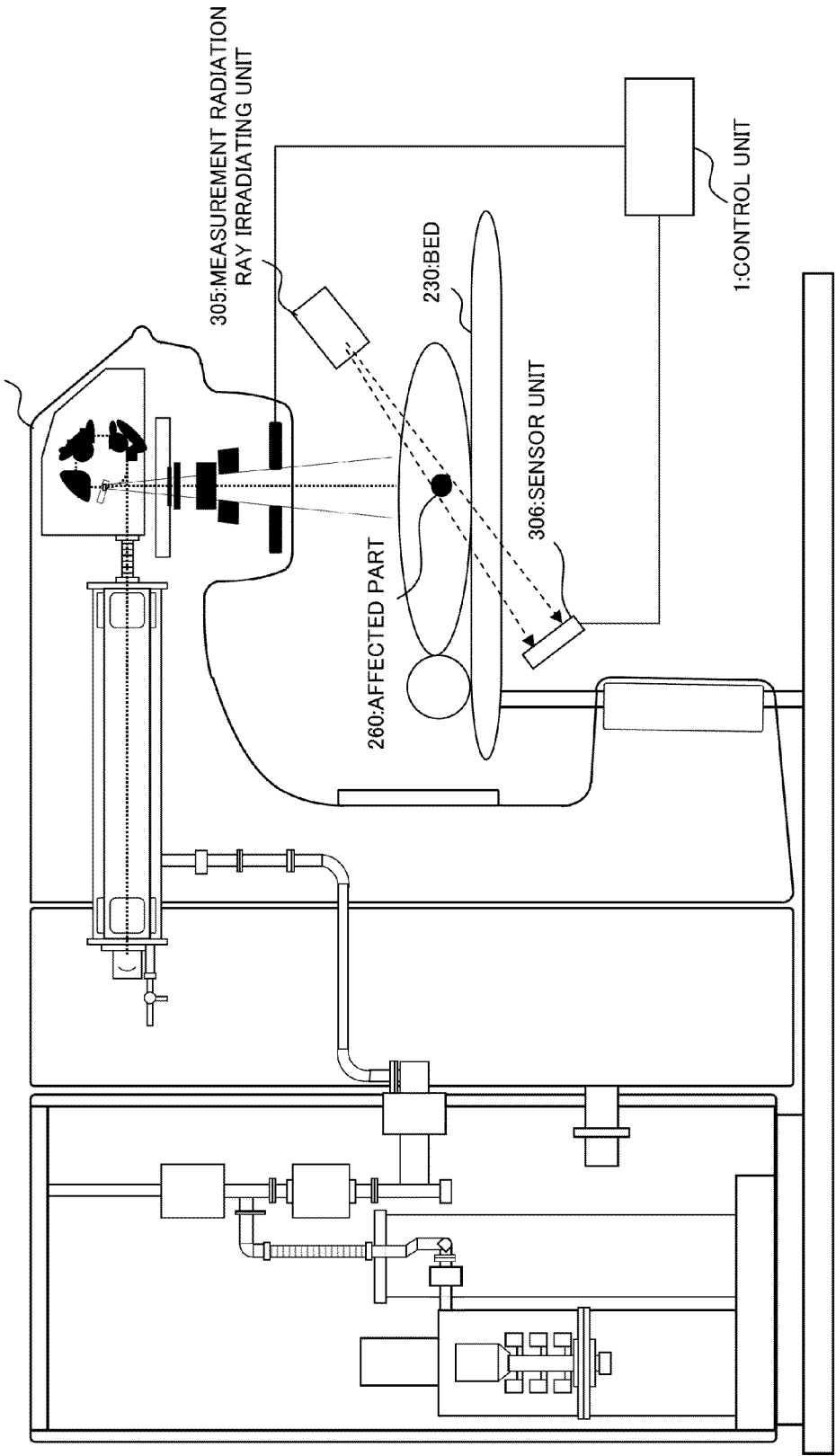
FIG. 1 is a diagram illustrating an example of a radiotherapy apparatus.

FIG. 1 is a diagram illustrating an example of a radiotherapy apparatus. The radiotherapy apparatus illustrated in FIG. 1 includes, for example, a control unit 1, a radiation ray irradiating device 90, a measurement radiation ray irradiating unit 305, and a sensor unit 306. For example, the radiotherapy apparatus can irradiate an affected part 260 of a patient located on a bed 230 with a therapeutic radiation ray.

At this time, the position, shape, size, and the like of the affected part 260 is temporally varied due to respiration or movement of the patient in some cases.

In this example, by causing the measurement radiation ray irradiating unit 305 to irradiate the vicinity of the affected part 260 with a radiation ray (for example, an X-ray) for transparent image photography and causing the sensor unit 306 to detect the radiation ray for the transparent image photography passing through the affected part 260, radiation transparent images (hereinafter, simply referred to as transparent images) of the vicinity of the affected part 260 are photographed and input to the control unit 1. Then, the control unit 1 measures (estimates) a temporal variation in the position, shape, size, and the like of a target portion of the affected part 260 or the like in the transparent images. Further, the control unit 1 may control the irradiation position and range of the therapeutic radiation ray irradiated from the radiation ray irradiating device 90 based on the measurement result. At this time, the control unit 1 may photograph and measure (estimate) the transparent images of the affected part 260 by a radiation ray passing through the affected part 260 using the therapeutic radiation ray irradiated from the radiation ray irradiating device 90 as an alternative of the measurement radiation ray, by using an electronic portal imaging device (EPID) or the like. Alternatively, the transparent images may be measured (estimated) combining both radiation rays. Further, the control unit 1 may match the irradiation position of the radiation ray with the affected part 260 by controlling the bed 230.

By integrating a plurality of transparent images for which photography directions are different, the position, shape, and size of a three dimensional affected part and a temporal variation (four-dimensional) in the position, shape and size can be simultaneously measured (estimated) in addition to a two-dimensional single-photographed surface of the affected part. At this time, the plurality of transparent images may be photographed by the same kind of fluoroscopic imaging apparatus or different kinds of fluoroscopic imaging apparatuses. Further, by integrating 4D-CT data obtained by photographing a movement of the affected part 260 in advance with transparent image data, three-dimensional measurement for a movement may be performed.

In an example to be described below, the position, shape, size, and the like of the affected part 260 are measured basically using the transparent images acquired by an X-ray simulator. The X-ray simulator can photograph transparent images of two frames every second. However, for example, an on board imager (OBI) can photograph transparent images of fifteen frames every second, and thus can realize higher-accuracy measurement.

(1.2) Example of Signal-Processing Device

Figure 2:
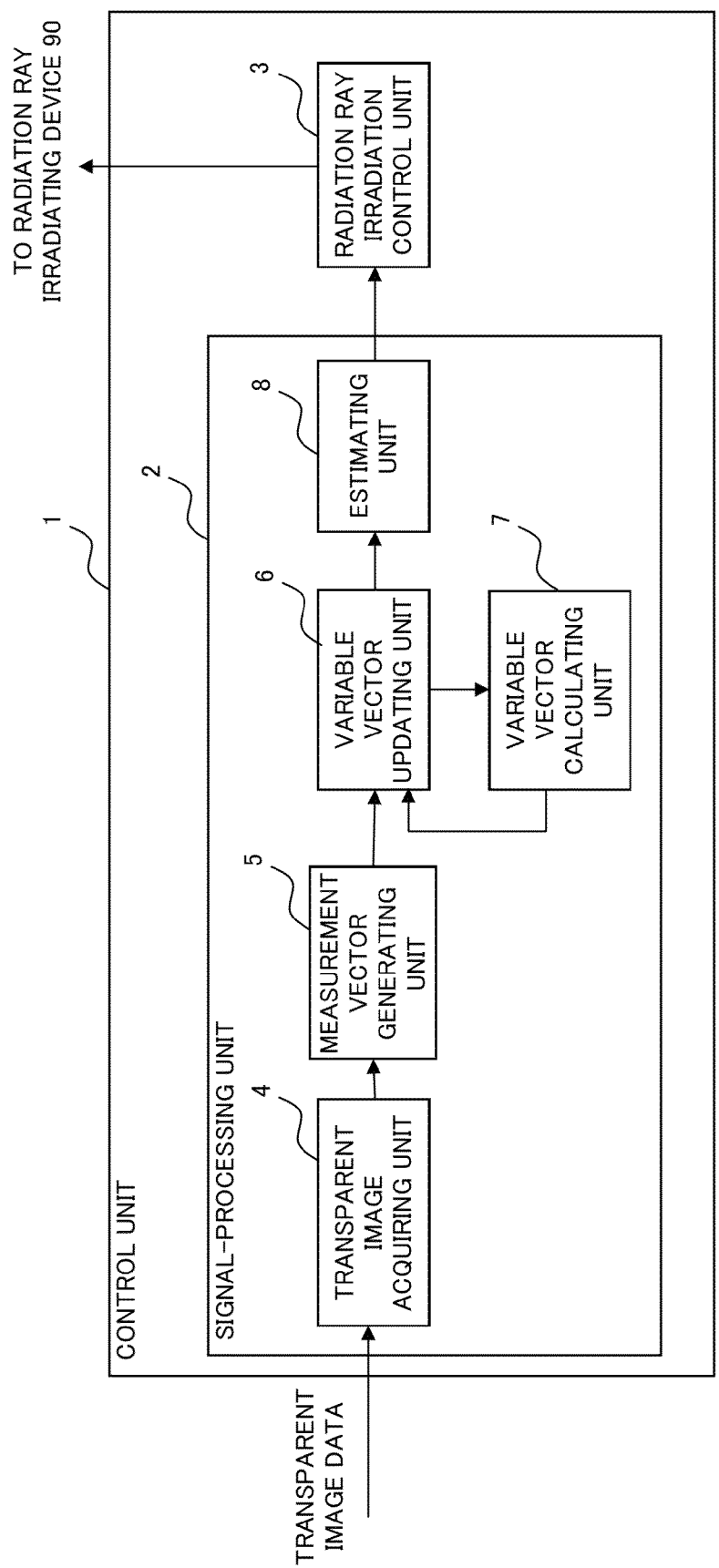
FIG. 2 is a functional block diagram illustrating a control unit illustrated in FIG. 1.

Here, the control unit 1 includes, for example, a signal-processing unit 2 and a radiation ray irradiation control unit 3, as illustrated in FIG. 2.

The signal-processing unit (signal-processing device) 2 measures (estimates) a temporal variation in the position and the like of the affected part 260 based on the transparent images photographed by the measurement radiation ray irradiating unit 305 and the sensor unit 306.

Therefore, the signal-processing unit 2 includes, for example, a transparent image acquiring unit 4, a measurement vector generating unit 5, a variable vector updating unit 6, a variable vector calculating unit 7, and an estimating unit 8. The operations of the transparent image acquiring unit 4, the measurement vector generating unit 5, the variable vector updating unit 6, the variable vector calculating unit 7, and the estimating unit 8 will be described in detail in (1.6) below. Hereinafter, the overview of the operation of each unit will be described.

The transparent image acquiring unit 4 acquires transparent images photographed by the measurement radiation ray irradiating unit 305 and the sensor 306. The transparent images are acquired at a plurality of times including a given time t. The transparent images generally include L (where, L is a natural number) target portions which are measurement (estimation) targets of the position, shape, size, and the like. That is, the transparent images include the L target portions and a background portion (here, (L+1) targets may be considered, or several targets may be considered as backgrounds and a plurality of backgrounds may be considered, since there is essentially no difference between the target and the background) other than the target portions can be expressed to be transparently superimposed.

The measurement vector generating unit 5 stores the transparent image by taking an interest in a region of M×N (where, M and N are natural numbers) pixels (pixels digitized from an analog image) or having a given representative value of the plurality of pixels in the transparent image at a time t when the transparent image is acquired by the transparent image acquiring unit 4, and generates luminance values (hereinafter, referred to as a density) of the MN interested regions and a measurement vector b (t, $t_1$, $t_2$, . . . , and $t_K$) (where, K is a natural number), which consists of (K+1) MN interested regions, of K transparent images acquired and stored at the times $t_1$, $t_2$, . . . , and $t_K$ prior to the time t. The transparent images may be stored by the transparent image acquiring unit 4.

The variable vector updating unit (updating unit) 6 updates variable vectors $I_{a1}$, $I_{a2}$, . . . , and $I_{aL}$ consisting of the luminance values respectively originating from the L target portions in the regions generated by the measurement vector generating unit 5 and a variable vector $I_b$ consisting of the luminance value of the background portion in the generated region based on background variable vectors $I_b(t_p)$ and target variable vectors $I_a(t_p)$ consisting of the measurement vector b and L variable vectors $I_{a1}(t_p)$, $I_{a2}(t_p)$, . . . , and $I_{aL}(t_p)$ of the interested regions of the transparent images at a time $t_p$ prior to the time t.

The variable vector calculating unit (calculating unit) 7 calculates the variable vectors I where f is a deterministic or stochastic function from the measurement vector b generated by the measurement vector generating unit 5, the variable vectors I including the target variable vectors $I_a$ and the background variable vector $I_b$ updated by the variable vector updating unit 6, and a coefficient matrix (function) A of (K+1)MN×(L+1) MN regarding the positions of the L target portions and the background portion at the times t estimated using the variable vectors I and the estimated positions of the L target portions and the background portion at the respective times being the K previous times $t_1$, $t_2$, . . . , and $t_K$.

$$PI=f(A,I,b) \quad \text{[Expression 2]}$$

The variable vector calculating unit 7 calculates the variable vectors I, for example, so that an evaluation value PI defined by the above expression is an appropriate value such as an optimum value.

The estimating unit 8 may estimate a temporal position variation of the target portions based on the target variable vectors $I_a$ in which a given initial value is set by the variable vector updating unit 6 and the target variable vectors $I_a$ updated by the variable vector updating unit 6, or may estimate the temporal position variation of the target portions based on the target variable vectors $I_a$ which have not been updated by the variable vector updating unit 6 and the target variable vectors $I_a$ updated by the variable vector updating unit 6. Further, the estimating unit 8 may estimate the shape, size, and the like of the targets based on the updated target variable vectors $I_a$.

The signal-processing unit 2 is configured such that the acquisition of the transparent image by the transparent image acquiring unit 4, the generation of the measurement vector b by the measurement vector generating unit 5, the updating of the variable vector I by the variable vector updating unit 6, and the calculation of the variable vector I by the variable vector calculating unit 7 are performed by shifting the time.

Information regarding the position, shape, size, and the like of a target portion, such as the affected part 260, measured by the signal-processing unit 2 is output to the radiation ray irradiation control unit 3.

The radiation ray irradiation control unit 3 controls an irradiation position and an irradiation range of the therapeutic radiation ray irradiated from the radiation ray irradiating device 90 or the position or the like of the bed 230 based on the information from the signal-processing unit 2.

(1.3) Verification of General Position Estimating Method

Figure 3:
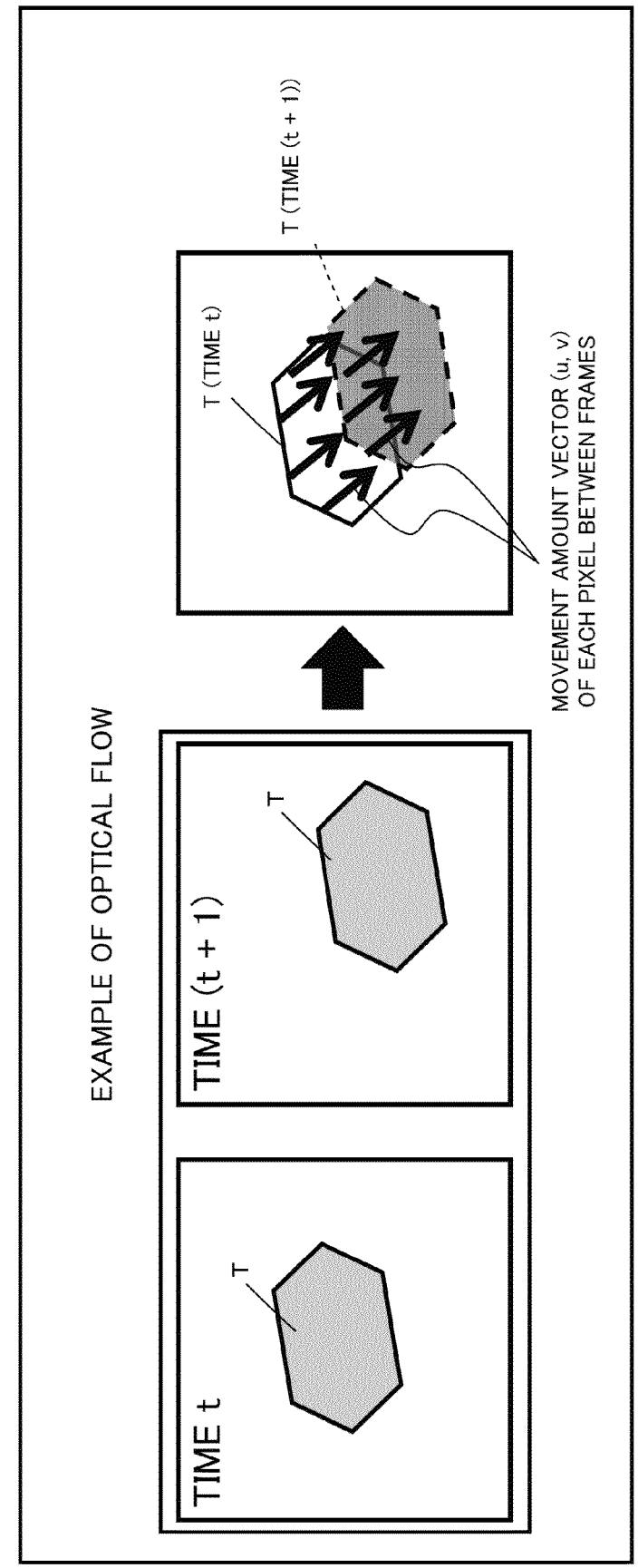
FIG. 3 is a diagram illustrating an example of an optical flow.

First, as illustrated in FIG. 3, optical flow extraction known as a general position estimating method is attempted from the above-described transparent images. In the optical flow extraction, a movement amount vector (u, v) is extracted for each pixel of a target portion (for example, the affected part 260) T between frames (also called moving image frames) of the transparent images photographed at different times. To facilitate the description, the number of target portions is assumed to be one (where, L=1) below.

FIG. 3 is a diagram illustrating a calculation example of the movement amount vector (u, v) between a target portion T at a time t (>0) and the target portion T at a discretely subsequent time (t+1). Here, the subsequent time (t+1) may be any future time of the time t and is simply referred to as a time (t+1) to facilitate the description.

First, a use example of a general block matching (BM) method will be described as an example of the optical flow extraction method. In the general optical flow extraction method such as the BM method or a gradient method, non-variation (uniformity) of the corresponding luminance value of each pixel of the target portion even by the movement of the target portion is a prerequisite.

The BM method is a method of extracting a movement displacement of each point of a target portion between frames by fully searching a given determined range (which may be a range of all the images) of a subsequent frame (also referred to as a subsequent frame) photographed at a time (t+1) using a region having a given size and including a given point of interest of a target portion in a frame prior to the subsequent frame (also referred to as a previous frame) photographed at a given time t and by setting a point, of which a relative position in a block is the same as that of the point of interest of the block of the subsequent frame in which an evaluation function of a difference or the like between the block and a template block of the previous frame is optimized, as a corresponding point.

Figure 4:
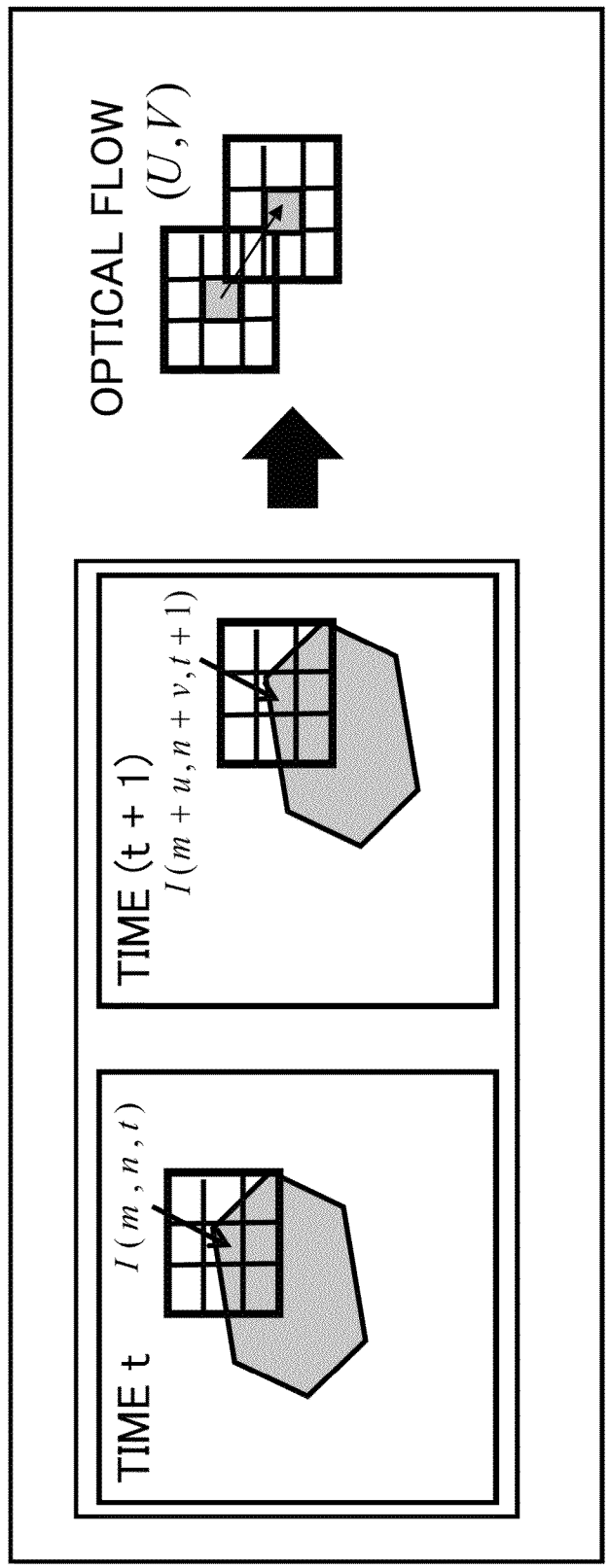
FIG. 4 is a diagram illustrating an example of a block matching (BM) method.

Specifically, for example, as illustrated in FIG. 4, first, in regard to M×N (in the example illustrated in FIG. 4, M=N=3) given template blocks including the target portion in the frame (previous frame) photographed at the time t, a given block in the previous frame and a block in which a difference valuation function is the minimum are searched from the blocks of the frame (subsequent frame) photographed at the time (t+1), and a movement amount vector (u, v) between the blocks is calculated.

The above-described calculation is performed as follows.

For example, when it is assumed that I (m, n, t) is the luminance value of a pixel at a position (m, n) of the target portion in the frame photographed at the time t and I (m, n, t+1) is the luminance value of the pixel at the position (m, n) of an extraction target in the frame photographed at the time (t+1), the mean square error (MSE) between the luminance value I (m, n, t) of the pixel in the previous frame and a luminance value I (m+u, n+v, t+1) of a pixel moved by the movement amount vector (u, v) from the pixel in the subsequent frame is defined by the following expression (a).

[Expression 3]

$$MSE(u, v) = \sum_m \sum_n \{I(m, n, t) - I(m+u, n+v, t+1)\}^2 \quad (a)$$

In this expression, {m, n} is a set of all the pixel positions present in the M×N blocks. In the BM method, for example, a flow (U, V) in which the MSE is the minimum is calculated for each block by the following expression (b).

[Expression 4]

$$(U, V) = \underset{u,v}{\operatorname{argmin}} MSE(u, v) \quad (b)$$

Figure 5:
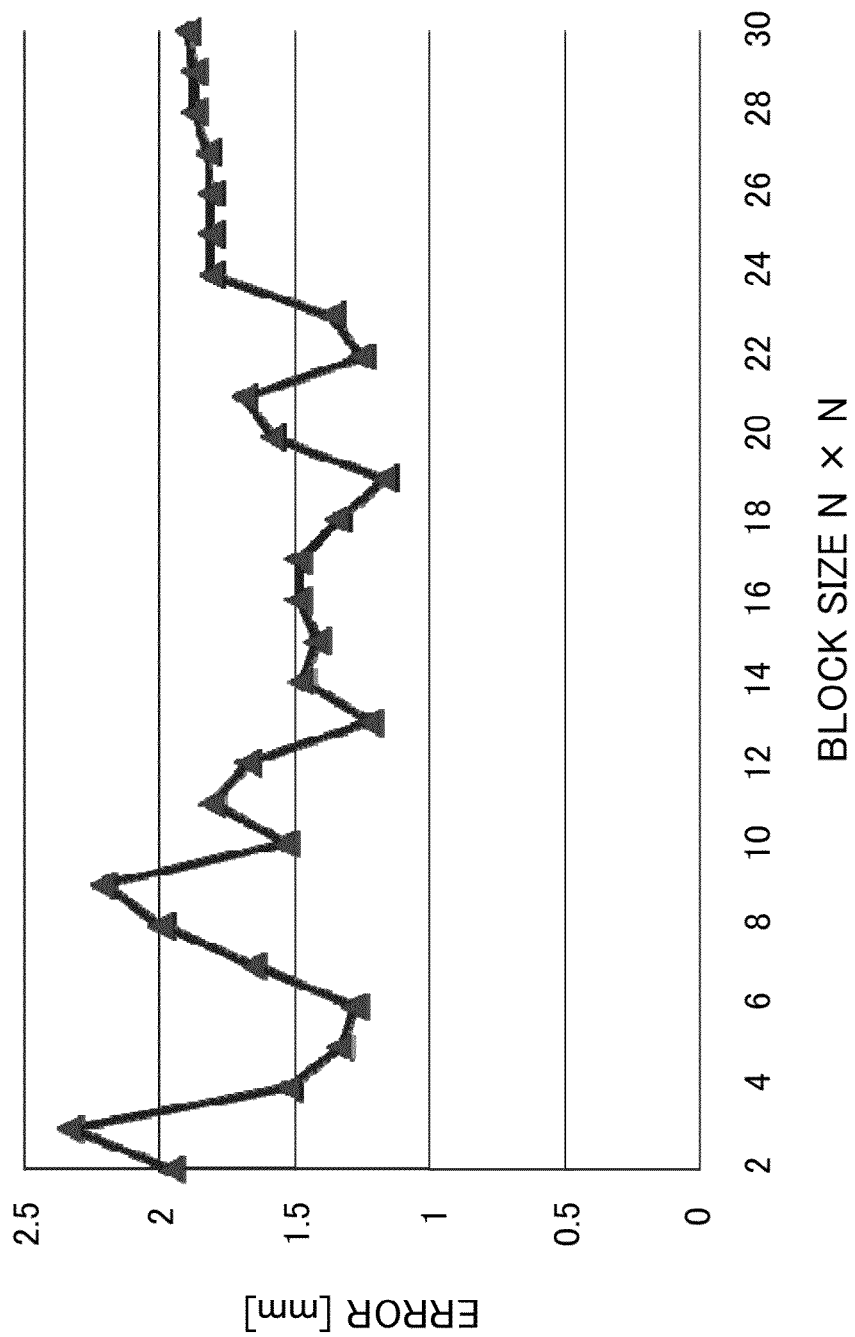
FIG. 5 is a diagram illustrating an error between a measured position of an affected part obtained by the BM method and an actual position of the affected part.

In practice, when the position of the affected part 260 is measured (estimated) using the BM method, a difference (estimation error) between the actual position and the estimated position of the affected part 260 is in the range from about 1.2 [mm] to about 2.4 [mm], as illustrated in FIG. 5. In this method, however, a contour portion with visually high contrast is manually set as a point of interest in a tumor portion of the affected part 260 of the target, since an improvement in accuracy is expected using a high-contrast portion, for example, by using a specific portion in which the contour of the target portion is clear. Further, a block size is set to a square N×N. In FIG. 5, the horizontal axis represents the size of the block size (N).

Thus, when the BM method is used in the position estimation of the affected part 260, a clinically required accuracy (for example, an estimation error is less than 1 [mm]) may not be achieved in spite of the efforts described above to improve the accuracy.

(1.4) Problem of General Position Estimating Method

As described above, the desired estimation accuracy (an error is less than 1 [mm]) may not be achieved in the BM method. The following two causes can be mainly considered.

First, there is a probability that a transparent image may be very unclear and a luminance value between frames may be different due to noise.

Second, since the luminance value of the affected part 260 is expressed by an integration value of the luminance value of the target portion itself and the luminance value of a background portion of the affected part 260 or the like in a transparent image, the prerequisite (that is, the luminance value of the target portion is not varied even by movement of the target portion) of the optical flow extraction method is not satisfied. Since this prerequisite is assumed in other general methods other than the optical flow extraction such as a phase restriction correlation method, dissatisfaction of the prerequisite is a more essential cause that results in deterioration in the accuracy.

Accordingly, a method of resolving each problem described above will be described below.

(1.5) Template Matching

Figure 6:
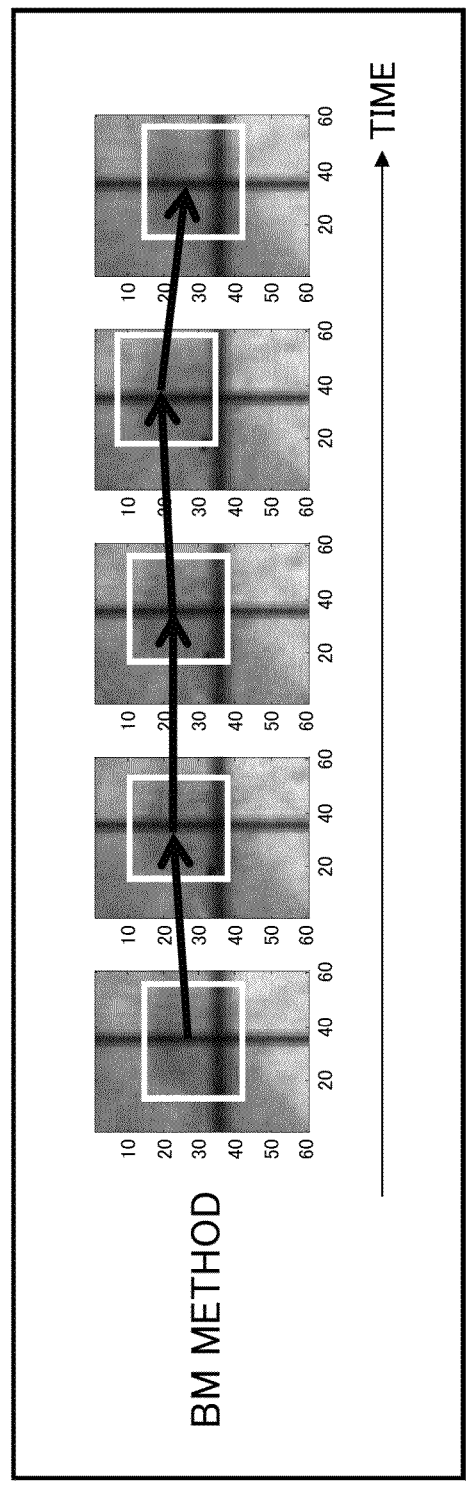
FIG. 6 is a diagram illustrating an overview of the BM method.

In the BM method, as illustrated in FIG. 6, the evaluation value such as a difference between a previous frame and a subsequent frame of a target portion is calculated. Therefore, when one of the transparent images in the previous and subsequent frames is unclear and the luminance value between the frames is different due to noise in the same target portion, the calculation accuracy of the evaluation value may deteriorate and a position estimation accuracy may thus deteriorate.

Accordingly, for example, a template matching (TM) method rather than the BM method can be used.

Figure 7:
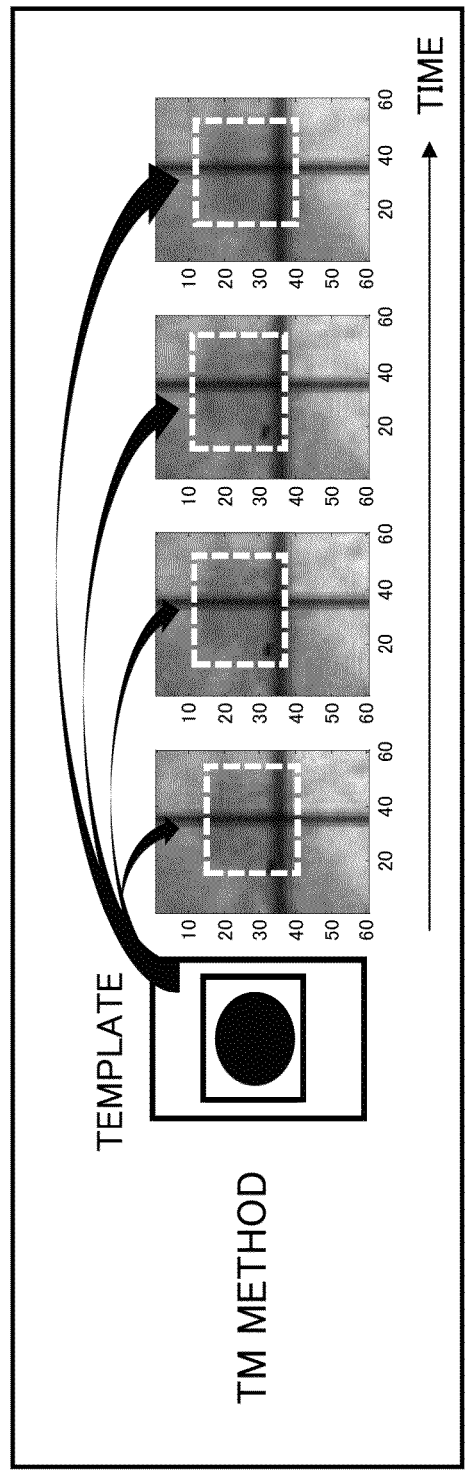
FIG. 7 is a diagram illustrating an overview of a template matching (TM) method.

As illustrated in FIG. 7, the TM method is a method of acquiring a template of a target portion in advance and searching for a range having the highest correlation with the template in a frame at each time. For example, a template used in the TM method can be acquired by determining a range having a luminance value equal to or greater than a predetermined value in a frame at a given time as a template. Further, a template may be determined based on the position, shape, size, and the like of the affected part 260 measured by another measurement apparatus (such as a CT or a magnetic resonance imaging (MRI)).

In the TM method, for example, the mean square error (MSE) between a luminance value $I_{temp}$ (m, n) of a template and a luminance value I (m+u, n+v, t) of a target portion in a frame at a time t is defined by the following expression (c).

[Expression 5]

$$MSE(u, v) = \sum_m \sum_n \{I_{temp}(m, n) - I(m + u, n + v, t)\}^2 \quad (c)$$

In the TM method, for example, a flow (U, V) in which the MSE is the minimum in the above expression (c) is calculated by the following expression (d).

[Expression 6]

$$(U, V) = \underset{u,v}{\operatorname{argmin}} MSE(u, v) \quad (d)$$

Thus, in the TM method, the position of the target portion is measured (estimated) based on the template of the target portion which does not receive the influence of the noise and the evaluation value of the target portion in each frame. Therefore, the estimation result rarely receives the influence of the unclearness of the transparent image, compared to the BM method in which there is a probability that both comparison targets may receive the influence of noise.

In the BM method, a density distribution has an influence on the evaluation value across the details of the target portion. In the TM method, however, the advantage that the evaluation value rarely receives the influence of a difference in the details of the target portion can be expected, for example, by using a template in which the density distribution is constant.

Further, in order to reduce the influence of noise, it is effective to perform a statistical process by adding a noise term in the expression (c).

(1.6) Separation of Density Distribution

Figure 8:
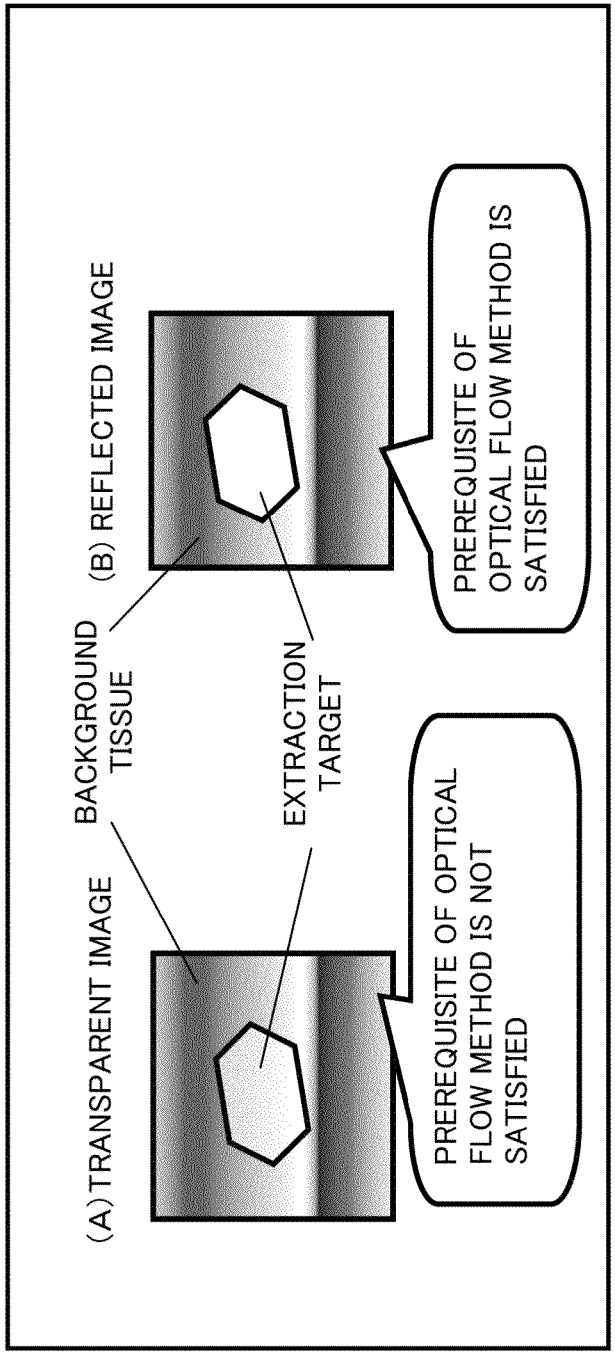
FIG. 8 is a diagram illustrating a difference between a transparent image and a reflected image.

As illustrated in FIG. 8(A), in the transparent image, the seeming luminance value of the target portion such as the affected part 260 is determined by an integration value of the luminance value of the original target portion and the luminance value of the background portion such as a neighborhood organ of the affected part 260.

Therefore, even when a part of the target portion is interested but the luminance value of the background portion overlapping the part temporally differs, the seeming luminance value of the part is not temporally constant. Accordingly, the prerequisite of the above-described optical flow method according to the related art is not generally satisfied in the transparent image.

On the other hand, as illustrated in FIG. 8(B), the luminance value of the target portion is not varied in accordance with the luminance value of the background portion in a normal image (referred to as a reflected image) rather than the transparent image. That is, when a part of the target portion in the reflected image is interested, the seeming luminance value of the part is constant in spite of the fact that the luminance value of the background portion overlapping the part temporally differs. Accordingly, the prerequisite of the above-described optical flow method according to the related art is generally satisfied in the reflected image.

Figure 9:
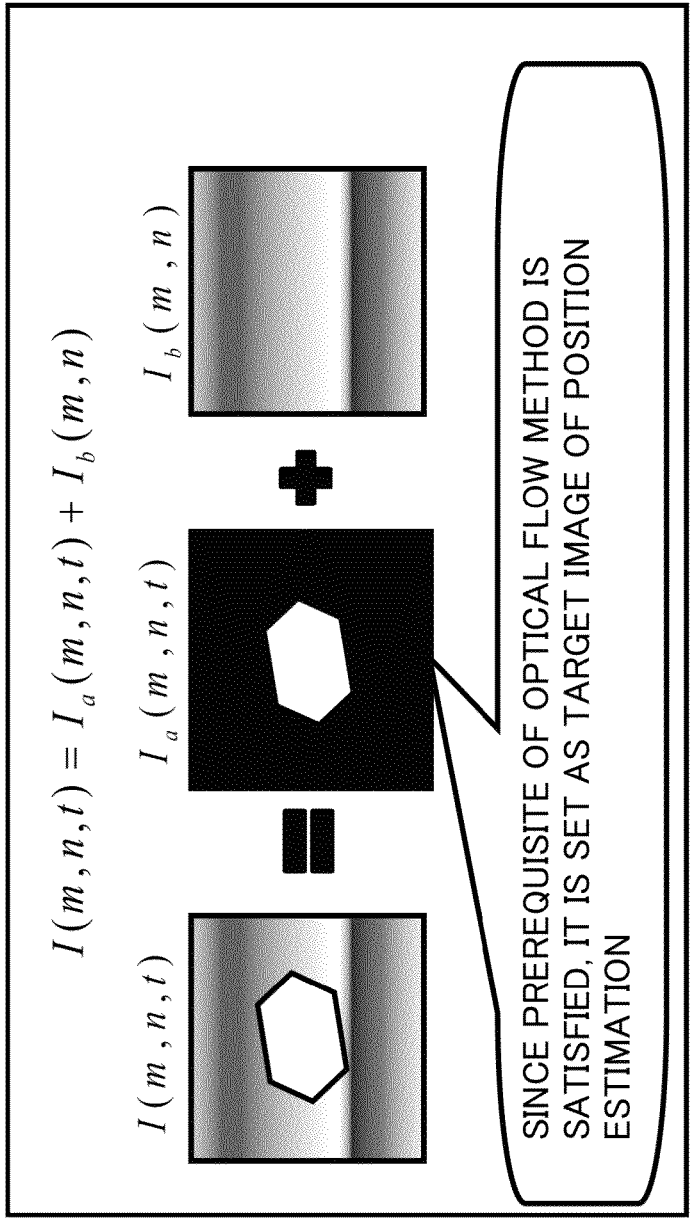
FIG. 9 is a diagram illustrating an example of a signal-processing method according to an embodiment.

Accordingly, in this example, as illustrated in FIG. 9, the seeming (measured) luminance value I (m, n, t) in the transparent image is separated into the original luminance value $I_a$ (m, n, t) of the temporally moved target portion and the luminance value $I_b$ (m, n, t) of the background portion moved independently of the target portion. To facilitate the description, it is assumed below that the number of target portions is one (L=1) and the luminance value is expressed as $I_b$ (m, n) in which the movement displacement of the background is 0 (that is, the background is still).

Since the prerequisite of the optical flow method is satisfied for the luminance value of the target portion separated from the transparent image (in this example, the separation is performed so that the prerequisite is satisfied), the position of the target portion can be measured (estimated) with high accuracy, as in the reflected image, by performing position estimation not on the luminance value I (m, n, t) measured in the transparent image but on the original luminance value $I_a$ (m, n, t) of the temporally moved target portion according to the TM method or the like. Further, since separation accuracy of the luminance value $I_a$ can be improved using information on the estimated position, not only the position of the target portion but also the shape, size, and the like of the target portion can be measured (estimated) with high accuracy by repeating each process.

Hereinafter, a separating method of this example will be described with reference to FIGS. 10 to 12.

Figure 10:
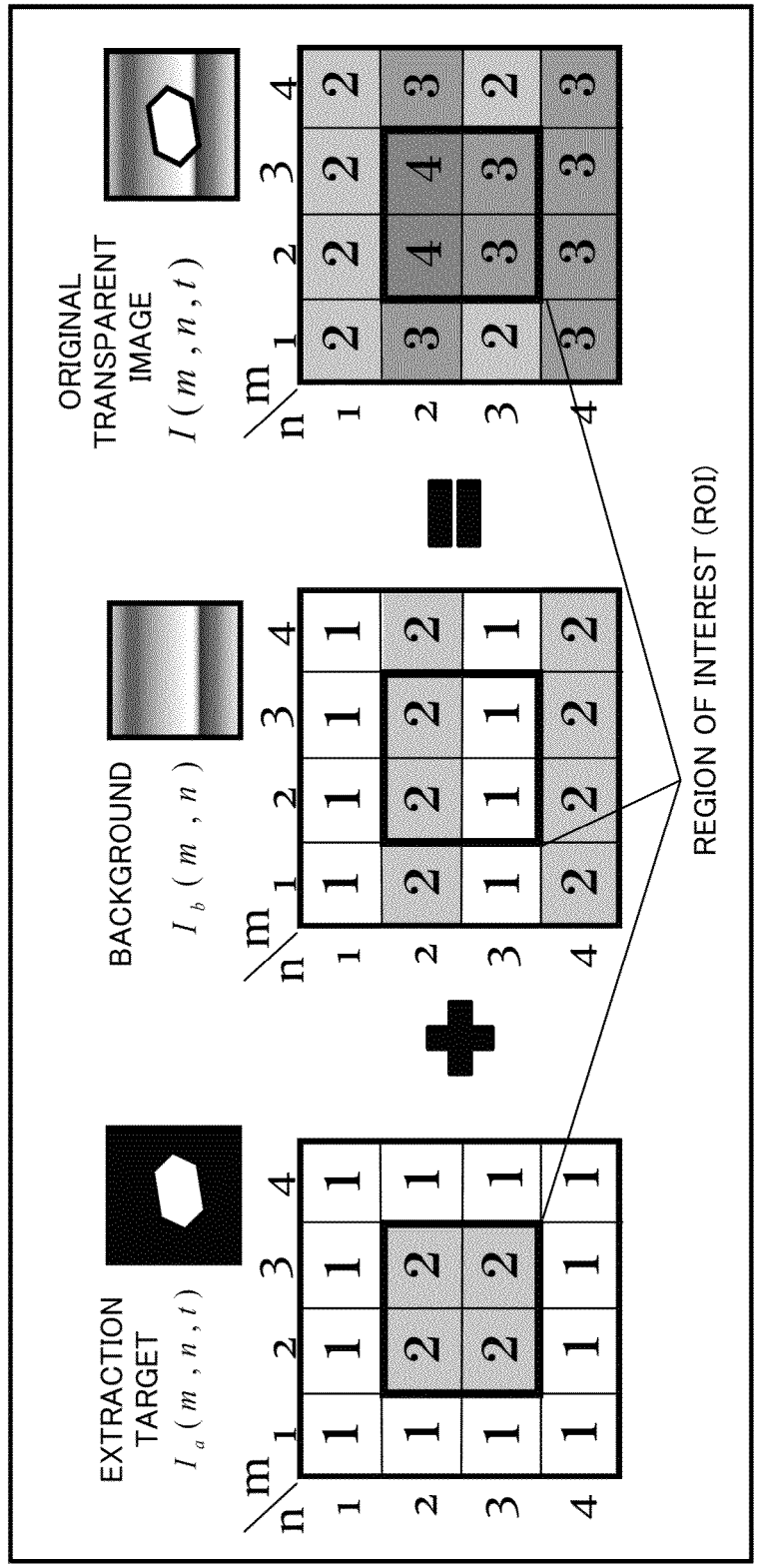
FIG. 10 is a diagram illustrating an example of the signal-processing method according to the embodiment.

First, as illustrated in FIG. 10, a luminance value vector (hereinafter, also referred to as a measurement vector) I (m, n, t) of a region (also referred to as a region of interest (ROI)) of the transparent image at the time t can be expressed to a luminance value vector $I_a$ (m, n, t) of the target portion and a luminance value vector $I_b$ (m, n) of the background portion by the following expression (e).

[Expression 7]

$$\begin{bmatrix} 1 & 0 & 0 & 0 & 1 & 0 & 0 & 0 \\ 0 & 1 & 0 & 0 & 0 & 1 & 0 & 0 \\ 0 & 0 & 1 & 0 & 0 & 0 & 1 & 0 \\ 0 & 0 & 0 & 1 & 0 & 0 & 0 & 1 \end{bmatrix} \begin{bmatrix} I_{a22} \\ I_{a23} \\ I_{a32} \\ I_{a33} \\ I_{b22} \\ I_{b23} \\ I_{b32} \\ I_{b33} \end{bmatrix} = \begin{bmatrix} 4 \\ 3 \\ 4 \\ 3 \end{bmatrix} \quad (e)$$

In the expression (e) above, $I_{amn}$, where "(m, n)={(2, 2), (2, 3), (3, 2), (3, 3)}," is a variable vector that represents the original luminance value of the target portion at the position coordinates (m, n) of each block in the ROI of the transparent image. Further, $I_{bmn}$, where "(m, n)={(2, 2), (2, 3), (3, 2), (3, 3)}," is a variable vector that represents the luminance value of the background portion at the position coordinates (m, n) of each block in the ROI of the transparent image.

As understood from FIG. 10, a solution of the equation expressed in the expression (e) is as follows.

$$\begin{bmatrix} I_{a22} \\ I_{a23} \\ I_{a32} \\ I_{a33} \\ I_{b22} \\ I_{b23} \\ I_{b32} \\ I_{b33} \end{bmatrix} = \begin{bmatrix} 2 \\ 2 \\ 2 \\ 2 \\ 2 \\ 1 \\ 2 \\ 1 \end{bmatrix}$$

However, the equation expressed in the expression (e) is an indefiniteness in which the number of independent equations for the number of unknown parameters lacks, and the variable vector $I_a$ ($I_{a22}$ to $I_{a33}$) of the target portion and the distribution ($I_{b22}$ to $I_{b33}$) of the variable vector $I_b$ of the background portion are not uniquely determined. This means that the components forming the density may not be generally separated from one transparent image.

Figure 11:
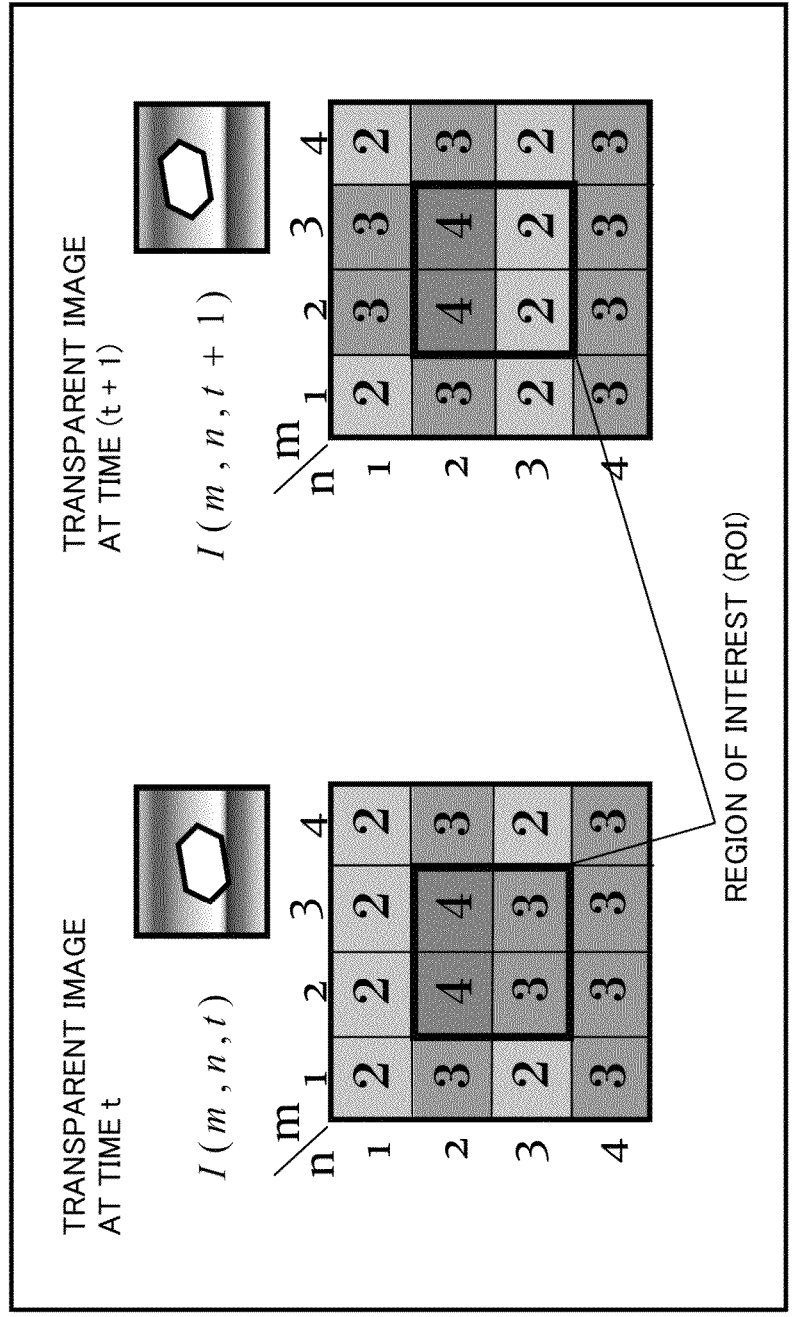
FIG. 11 is a diagram illustrating an example of the signal-processing method according to the embodiment.

Therefore, as illustrated in FIG. 11, by temporally integrating the measurement frame acquired at the time t and the measurement frame acquired at another time (continuously, referred to as (t+1) to facilitate the description), the measurement vector I of each ROI is expressed with the variable vector $I_a$ of the target portion and the variable vector $I_b$ of the background portion by the following expression (f).

[Expression 8]

$$\begin{bmatrix} 1 & 0 & 0 & 0 & 1 & 0 & 0 & 0 \\ 0 & 1 & 0 & 0 & 0 & 1 & 0 & 0 \\ 0 & 0 & 1 & 0 & 0 & 0 & 1 & 0 \\ 0 & 0 & 0 & 1 & 0 & 0 & 0 & 1 \\ 0 & 1 & 0 & 0 & 1 & 0 & 0 & 0 \\ 0 & 0 & 0 & 0 & 0 & 1 & 0 & 0 \\ 0 & 0 & 1 & 0 & 0 & 0 & 1 & 0 \\ 0 & 0 & 0 & 0 & 0 & 0 & 0 & 1 \end{bmatrix} \begin{bmatrix} I_{a22} \\ I_{a23} \\ I_{a32} \\ I_{a33} \\ I_{b22} \\ I_{b23} \\ I_{b32} \\ I_{b33} \end{bmatrix} = \begin{bmatrix} 4 \\ 3 \\ 4 \\ 3 \\ 4 \\ 2 \\ 4 \\ 2 \end{bmatrix} \quad (f)$$

In the expression (f) above, a left matrix of the left-hand side is a coefficient matrix (function) A and is, for example, a matrix determined by the positions of the target portions at different times t and (t+1). The right matrix of the left-hand side is a variable vector I that represents the density of the target portion and the background portion of the ROI at the time t. The matrix of the right-hand side is a measurement vector b that represents the luminance values measured in the ROIs of the transparent images acquired at the different times t and (t+1). In this example, the transparent image is defined to have 4×4 pixels, that is, sixteen pixels or any sixteen representative values of a plurality of pixels. The ROI is defined to have 2×2 pixels, that is, four ("MN=4" from "M=2" and "N=2") pixels. Therefore, the coefficient matrix collected at two times is an 8×8 matrix, since "(K+1) MN=8" and "(L+1) MN=8" are calculated from "K=1" and "L=1." The variable vector I is merely an 8×1 matrix. The size of each row and column is varied depending on the number of pixels (or representative values) of the transparent image, the number of pixels (or representative values) of the ROI, the number of target portions, and the number of previous times to be integrated.

Here, when the coefficient matrix A becomes a full rank, the variable vector I associated with the coefficient matrix A is uniquely calculated.

In practice, however, since how the target portion is moved is not clear at the different times t and (t+1), that is, the coefficient matrix A (in particular, a 4×4 submatrix $\{a_{ij}\}$ formed by extracting $1^{st}$, $2^{nf}$ and $4^{th}$ columns of $5^{th}$, $6^{th}$, $7^{th}$, and $8^{th}$ rows of the coefficient matrix A, "i=5, 6, 7, 8, j=1, 2, 3, 4" is set, $a_{ij}$ is a component at an $i^{th}$ row and a $j^{th}$ column of the matrix A, and the background is assumed to be still, but j=1, . . . , 8 when the background is also moved) is not clear, the coefficient matrix A is estimated in this example.

In regard to each component of the variable vector I associated with the coefficient matrix A, for example, the luminance values of the template generated by the above-described template generating method are set as the initial values. However, since the luminance values are merely assumed value, the luminance values are generally different from actual values.

In this example, the estimation accuracy of the coefficient matrix A and the variable vector I described above is improved by starting given initial values and repeatedly updating the initial values using the estimated values.

Figure 12:
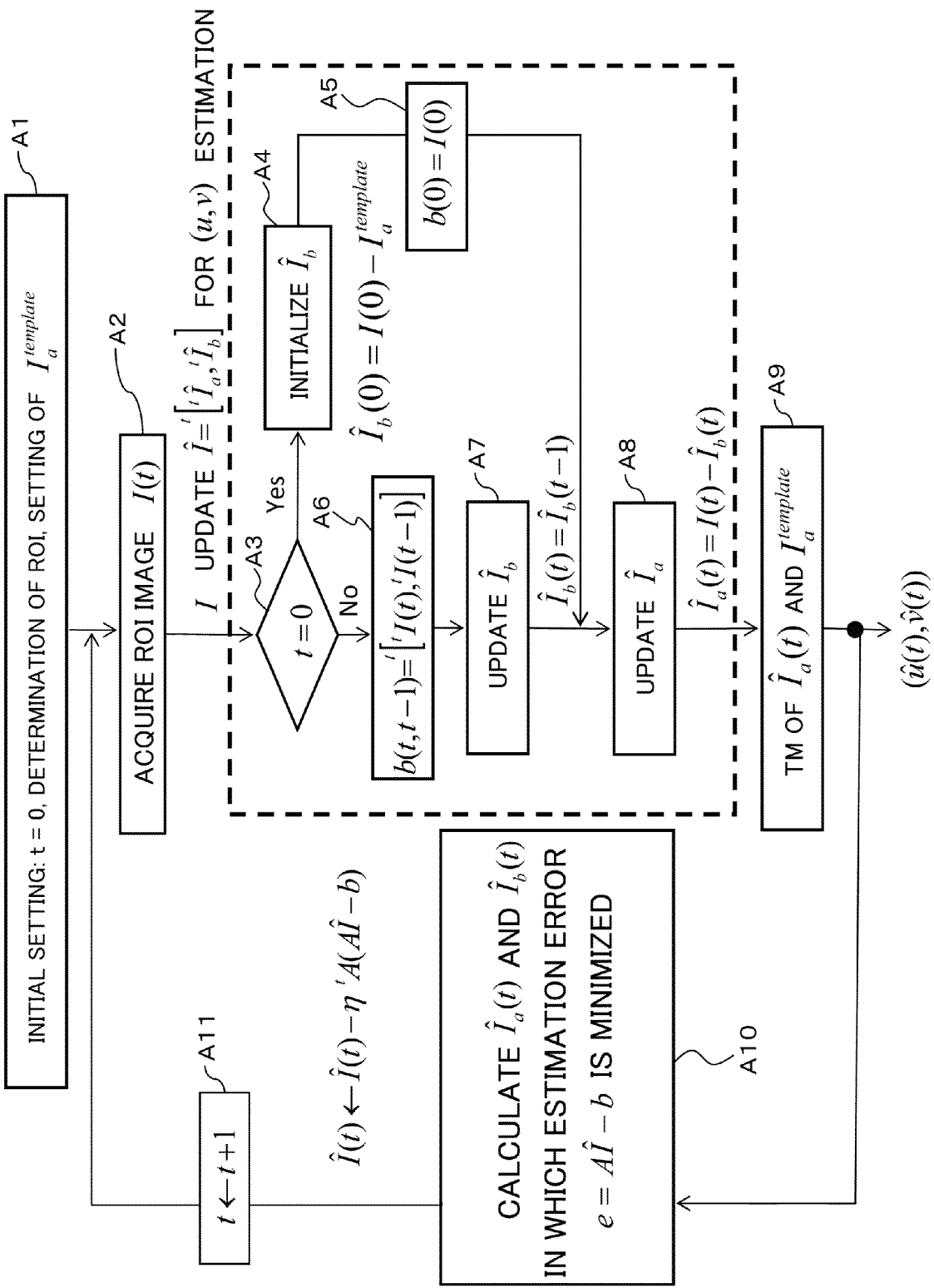
FIG. 12 is a diagram illustrating an example of the signal-processing method according to the embodiment.

FIG. 12 is a flowchart illustrating an operation of this example.

As illustrated in FIG. 12, first, the signal-processing unit 2 sets, as initial setting, a region of interest (ROI) in the transparent image by substituting "0" to a time parameter t. Then, the variable vector updating unit 6 sets, for example, the luminance value vector $I_a^{template}$ of the template of the target portion as the initial value of the variable vector $I_a$ (step A1).

Here, the ROI is preferably set to include the target portion such as the affected part 260. For example, a region always including the target portion can be set as an ROI automatically or manually through visual observation based on CT or MRI images or the like obtained by separately photographing the target portion and the outline of a movement range of the target portion. Alternatively, by assuming that a portion (range) including a luminance value equal to or greater than a predetermined value in transparent images acquired in advance at given times is the target portion, the range in which the target portion moves can be estimated and a region including the range can be set as an ROI.

In regard to the luminance value vector $I_a^{template}$ of the template, for example, the variable vector updating unit 6 can set a portion as the template of the target portion by assuming, as the target portion, the portion (range) having the luminance value equal to or greater than the predetermined value in the transparent images obtained by roughly extracting the contour of the target portion automatically or manually and visually based on the CT or MRI images obtained by separately photographing the target portion or acquired at given times. Further, the luminance value vector $I_a^{template}$ can be calculated by setting the luminance value of the extracted portion as an appropriate constant value or based on information regarding lightness which the template has.

Next, the transparent image acquiring unit 4 acquires the transparent image in regard to the target portion at the time t. That is, the transparent image acquiring unit 4 and the measurement vector generating unit 5 acquire a luminance value vector I(t) in the ROI set in step A1 from the transparent image acquired at the time t (step A2).

Then, the variable vector updating unit 6 performs an updating process on the following value which is the estimated value of the variable vector I used to estimate the movement amount vector (u, v) of the target portion in the subsequent steps A3 to A8 (see a dashed line in FIG. 12).

$$\hat{I} = {}^t[{}^t\hat{I}_a, {}^t\hat{I}_b]$$

In FIG. 12, a hat sign attached to each variable indicates that the variable is an estimated value. Further, a matrix $^tA$ is a transposed matrix of a matrix A. In the following description, the dash sign "'" is used instead of the hat sign in some cases due to the denotative restriction.

In the updating process, the variable vector updating unit 6 first determines whether the time parameter t satisfies "t=0" (step A3).

When the variable vector updating unit 6 determines that the time parameter t satisfies "t=0" (Yes route of step A3), the variable vector updating unit 6 initializes a variable vector $I_b'$ (step A4). The initialization of the variable vector $I_b'$ in step A4 may be performed, for example, by subtracting the luminance value vector $I_a^{template}$ of the template from the measurement vector I(0) of the time "t=0" generated by the measurement vector generating unit 5 and setting the subtraction result to a variable vector $I_b'(0)$.

The measurement vector generating unit 5 sets the measurement vector I(0) of the time "t=0" to b(0) (step A5).

Conversely, when the variable vector updating unit 6 determines that the time parameter t does not satisfy "t=0" (No route of step A3), for example, the measurement vector generating unit 5 sets the ROIs of the acquired transparent images as a region of M×N pixel (or representative value) and generates a measurement vector b (t, t−1) of 2MN pixels (or representative values) based on the luminance values of the MN ROIs and the luminance values of the MN pixels (or representative values) of the ROIs of the transparent images acquired at the time (t−1), as described above (step A6). For example, the measurement vector generating unit 5 may measure the lightness of the vicinity of a unit area of each block in the ROI of the transparent image and calculate the luminance values based on the measurement result. Then, the variable vector updating unit 6 updates the variable vector $I_b'$ (step A7). The updating of the variable vector $I_b'$ in step A7 is performed, for example, by setting the value of the variable vector $I_b'$ calculated at the previous time by the variable vector calculating unit 7 to the variable vector $I_b'$ at the subsequent time.

Next, the variable vector updating unit 6 updates a variable vector $I_a'$ (step A8). The updating of the variable vector $I_a'$ in step A8 is performed, for example, by subtracting the variable vector $I_b'$ initialized or updated in step A4 or A7 from the measurement vector I(t) of the time t generated by the measurement vector generating unit 5 and setting the subtraction result to the variable vector $I_a'$.

Then, for example, the estimating unit 8 calculates (estimates) an estimated value (u'(t), v'(t)) of the movement amount vector of the target portion by applying the TM method or the gradient method between the luminance value vector $I_a^{template}$ set in step A1 and the variable vector $I_a'$ updated in step A8 (step A9). At this time, the estimating process may be performed at high speed by assuming the target portion as a rigid body in which all of the points of the target portion have the same movement amount, or the estimating process may be performed precisely by assuming the target portion as a non-rigid body in which all or some of the points of the target portion have different movement amounts from the movement amounts of the other points. To facilitate the description, the target portion is assumed as the rigid body. Further, for example, the estimating unit 8 may calculate (estimate) the estimated value (u'(t), v'(t)) of the movement amount vector of the target portion by applying the BM method or the gradient method between the variable vector $I_a'$ before the updating of step A8 and the variable vector $I_a'$ after the updating of step A8, or may calculate (estimate) in accordance with the phase restriction correlation method with the luminance value vector $I_a^{template}$ or the variable vector $I_a'$ after the updating of step A8 or a method using a particle filter.

Next, the variable vector calculating unit 7 estimates and updates the coefficient matrix A based on the estimated value (u'(t), v'(t)) of the movement amount vector estimated by the estimating unit 8. That is, the variable vector calculating unit 7 (function updating unit) has a function of estimating and updating the coefficient matrix (function) A based on the variable vector $I_a$ in which the initial value is set and the updated variable vector $I_a$. Alternatively, the variable vector calculating unit 7 has a function of estimating and updating the coefficient matrix A based on the variable vector $I_a$ before the updating and the variable vector $I_a$ after the updating.

When t is not equal to 0, the variable vector calculating unit 7 calculates I(t) in which the square of each component of the error e defined in, for example, the following expression (g) is the minimum (step A10).

$$e = A\hat{I} - b(I) \ldots (g) \quad \text{[Expression 9]}$$

Here, the true value of the matrix A is calculated. Further, when the coefficient matrix A is a full rank, a precise solution I of a simultaneous equation satisfying the error "e=0" can easily be calculated by calculating the inverse matrix of the matrix A. However, in practice, the matrix A is the estimated value, as described above. Even when the coefficient matrix A becomes the full rank and the precise solution is calculated, the precise solution is not guaranteed to accord with $I_a$ and $I_b$ into which the luminance value is separated. Accordingly, in this example, the precise solution is not calculated, but a separation density is estimated by using an optimization method or the like.

As a method of minimizing the square of the error e, for example, an optimization method such as a steepest descent method, a conjugate gradient method, a Newton method can be used or a so-called calculation intelligence method such as an artificial neuron network, a fuzzy theory, or an evolutional computation theory can be used. A stochastic optimization method can be used by adding a statistical noise term to an error function. This method is an effective method in an unclear image in which much noise is present. Further, in the many images originating from the tumor portion to be targeted in this example, only the target is present, and the luminance of a portion other than the target portion is 0. Therefore, in the estimated $I'_a$, the value of a pixel, a luminance value of which is less than a given value may be subjected to a threshold value process or the like to remove the noise. Thus, an accumulation reduction advantage of the estimation error during the optimization can be expected.

For example, the following expression (h) is used, when the I(t) in which the square of each component of the error e is minimized using the steepest descent method is calculated.

$$\hat{I}(t) \leftarrow \hat{I}(t) - \eta^t A(A\hat{I}(t) - b(t, t-1)) \ldots (h) \quad \text{[Expression 10]}$$

In the expression (h), b (t, t−1)=$^t[^tI(t-1), ^tI(t)]$=b(I) and η is a positive coefficient that indicates a change ratio.

That is, the variable vector calculating unit 7 calculates the variable vector I by which an evaluation index such as the error e is suited by using the optimization method based on the estimated coefficient matrix A.

The signal-processing unit 2 repeatedly performs the processes of steps A2 to A11 by incrementing the value of the time t (step A11).

That is, the signal-processing unit 2 of this example is configured such that the acquisition of the transparent image by the transparent image acquiring unit 4, the generation of the measurement vector b by the measurement vector generating unit 5, the updating of the variable vectors $I_a$ and $I_b$ by the variable vector updating unit 6, and the calculation of the variable vectors $I_a$ and $I_b$ by the variable vector calculating unit 7 are performed by shifting the time.

Accordingly, the variable vector updating unit 6 updates the variable vectors $I_a$ and $I_b$ using the variable vectors $I_a$ and $I_b$ calculated by the variable vector calculating unit 7, respectively.

As described above, according to the signal-processing method of this example, the target portion and the background portion can be separated from the transparent image. Therefore, by tracking the position of the separated target portion, the position of the target portion can be measured (estimated) with high accuracy. The shape, size, and the like of the target portion can be measured (estimated) with high accuracy by the separation.

(1.7) Experiment Examples

Figure 13:
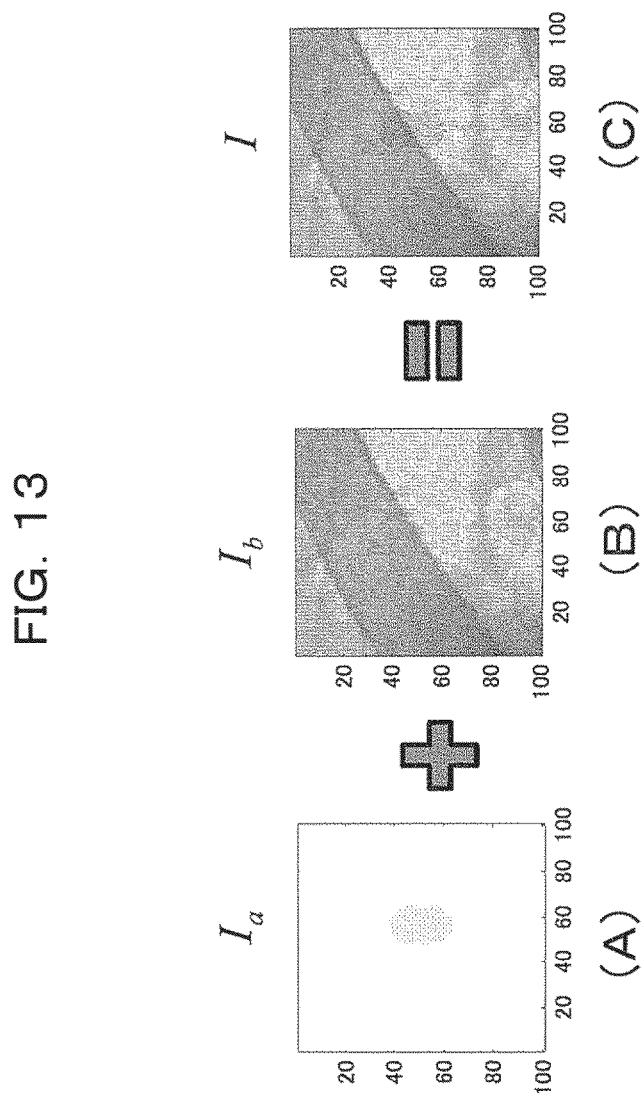
FIG. 13(A) is a diagram illustrating an example of a true value image of a target (tumor) portion.
FIG. 13(B) is a diagram illustrating an example of a true value image of a background portion.
FIG. 13(C) is a diagram illustrating an example of a transparent image of phantom data.
Figure 14:
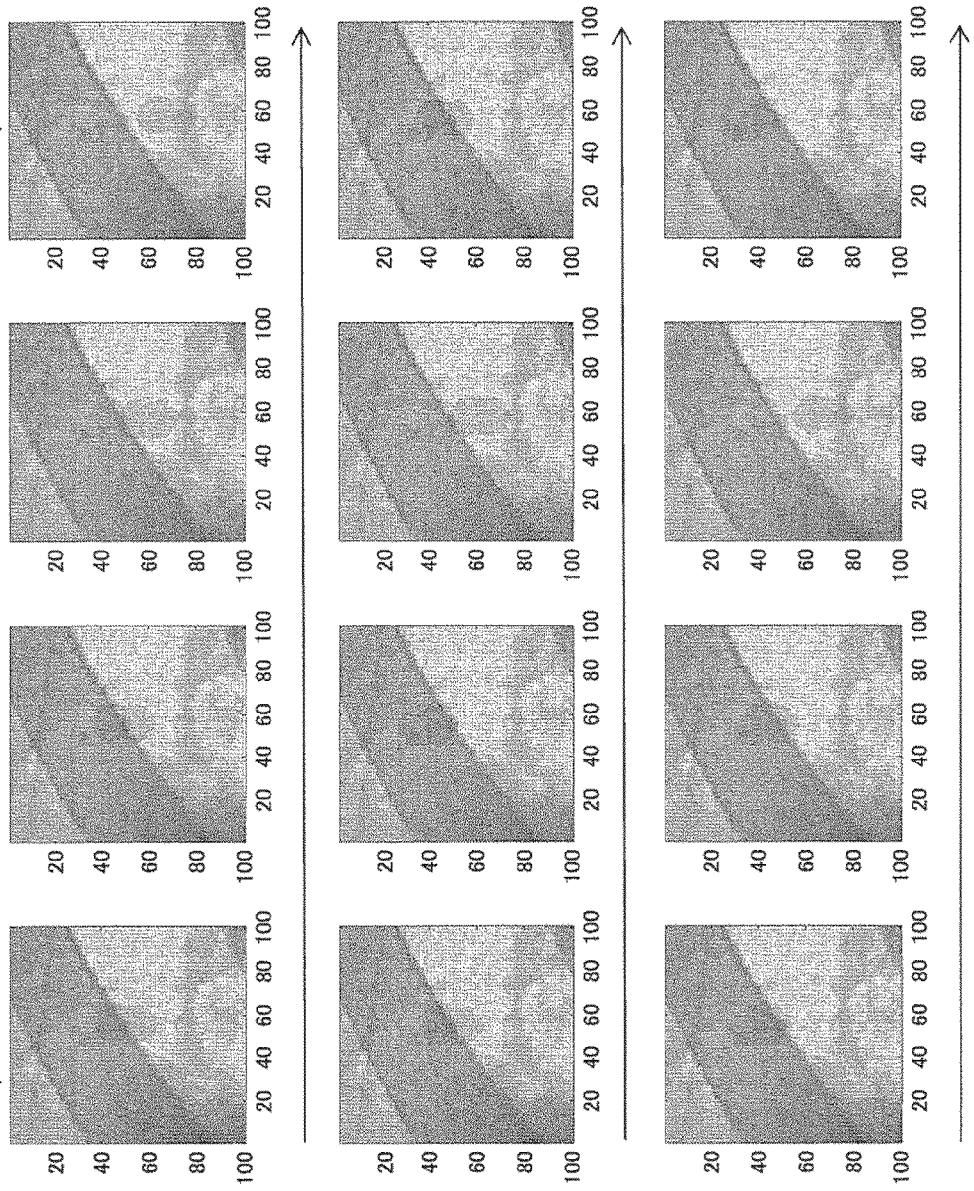
FIG. 14 is a diagram illustrating examples of transparent images of the phantom data.

Fist, an experiment result of using phantom data for which a separation density of a true value is known will be described. The phantom data is transparent image data, as illustrated in FIG. 13(C), obtained by setting a transparent image, as illustrated in FIG. 13(B), which has a ROI size of 100×100 and has no target tumor, as a background and integrating the tumor image, as illustrated in FIG. 13(A), which is artificially moved, to the background. FIG. 14 is a diagram illustrating a change example of the frame of the phantom data over time. In the example illustrated in FIG. 14, transparent images of 12 frames appropriately selected from a total of 110 frames are arranged in the time-series order from the left upper side to the right lower side. A tumor is moved in the vicinity of the middle of the ROI mainly in a vertical direction, and thus a movement of an actual lung tumor is simulated.

Figure 15:
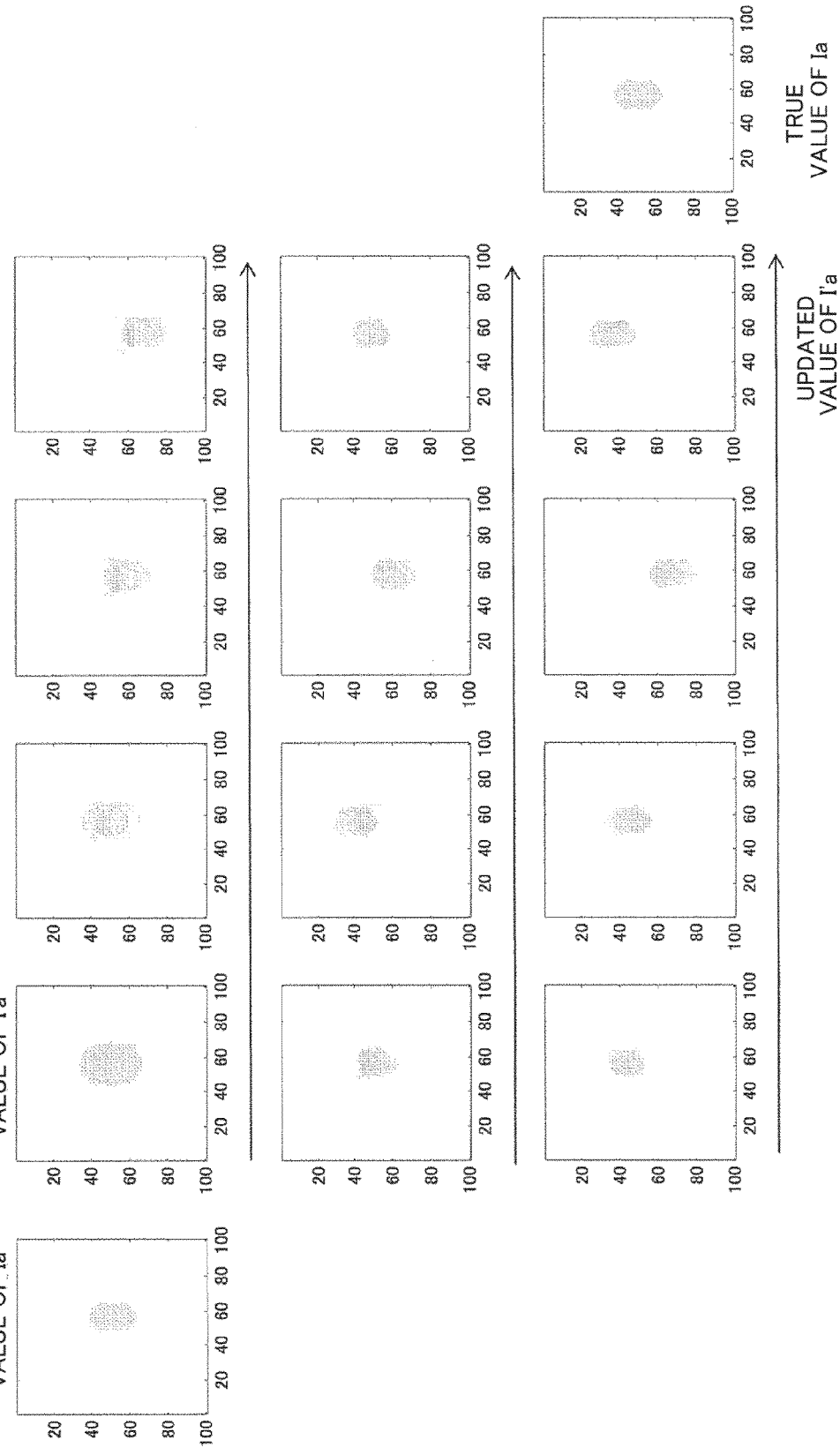
FIG. 15 is a diagram illustrating target portions separated from the transparent images illustrated in FIG. 14.
Figure 16:
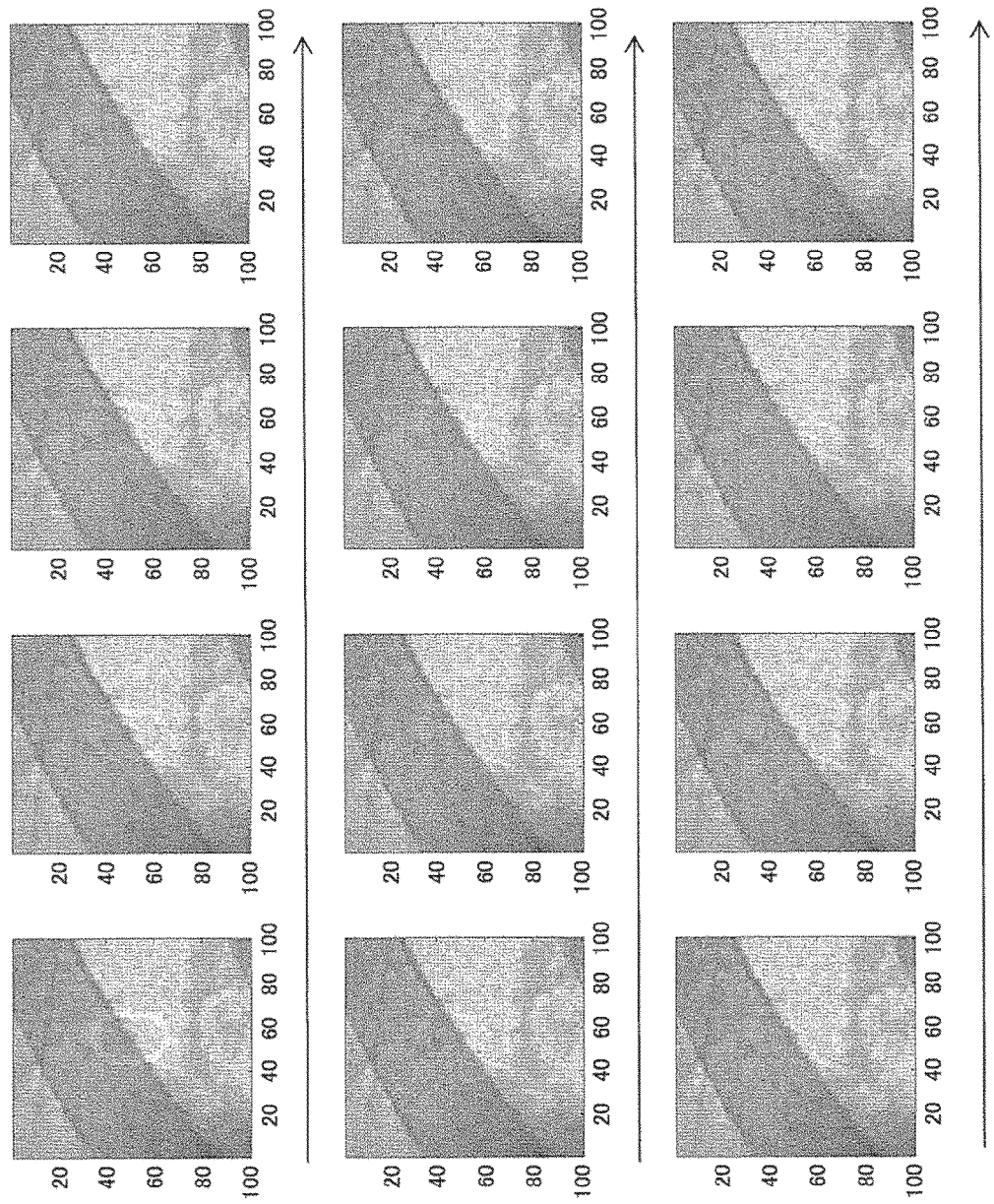
FIG. 16 is a diagram illustrating background portions in which the target portions illustrated in FIG. 15 are separated from the transparent images illustrated in FIG. 14.
Figure 17A:
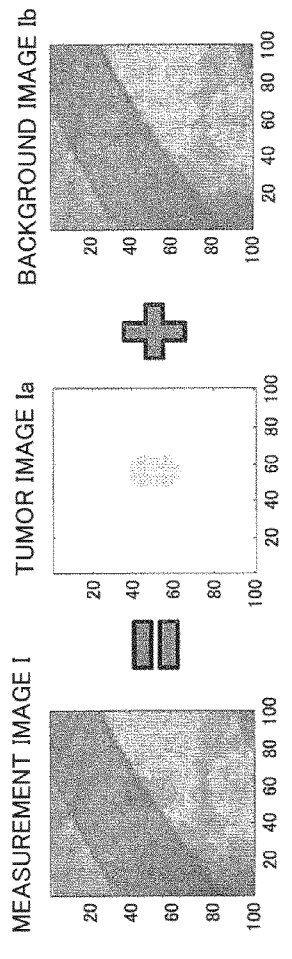
FIGS. 17A to 17C are diagrams illustrating comparison between target images separated from the transparent images and background images.
Figure 17B:
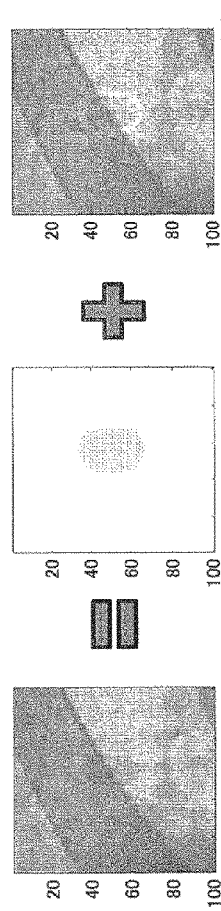
Figure 17C:
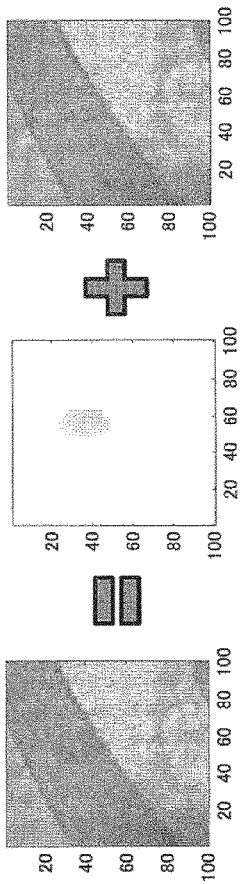

The signal-processing method of this example is applied to each frame illustrated in FIG. 14. As illustrated in FIGS. 15 and 16, even when an initial value quite different from the true value is appropriately set manually, both a target portion and a background portion can be separated with accuracy over time. In particular, as illustrated in FIG. 15, it can be understood that the tumor image almost similar to the tumor image illustrated in FIG. 13(A) is developed over time from the initial value appropriately set manually and visually and is extracted to be separated. The error of the initial value is 300 pixels or more among 10000 pixels with the ROI size and the density difference is 20 per pixel. The experimental example succeeds in that the error is 0 pixel and the density difference per pixel is decreased up to about average 0.1 or less in the final frame, and thus the target portion and the background portion are separated with high accuracy. Since the shape of the target tumor is also completely separated, the remaining error is merely a small error of the density value in the shape of the target tumor. This can be confirmed from the fact that the background images, as illustrated in FIG. 16, in which the tumor is separated, accord with the image illustrated in FIG. 13(B). A comparison example between a true value image and the separation result obtained by repeating the setting of the initial value and the updating is illustrated in FIGS. 17A to 17C. Since the shape, size, and the like of a tumor in the initial image (FIG. 17B) are considerably different from those in a true value image (FIG. 17A), the influence on the background image can be clearly comprehended. However, the shape and the size of the tumor are accurately separated in a separation result image (FIG. 17C). Further, a slight error remains in the density distribution, but new tracking can be realized with high accuracy by repeatedly applying the signal-processing method of this example. With such an error, it is difficult to view the influence on the background image.

At this time, the position of the target portion is measured in the finally separated $I_a$ using the TM method as an example of the position estimating method. Since the estimation error is almost 0, an accurate position estimation result can be obtained. Likewise, when the BM method according to the related art is applied to the phantom data, an average error is about 3 [mm] due to the influence of a costa contour or the like with high contrast in the background image. Accordingly, effectiveness of the signal-processing method can be confirmed.

Figure 18:
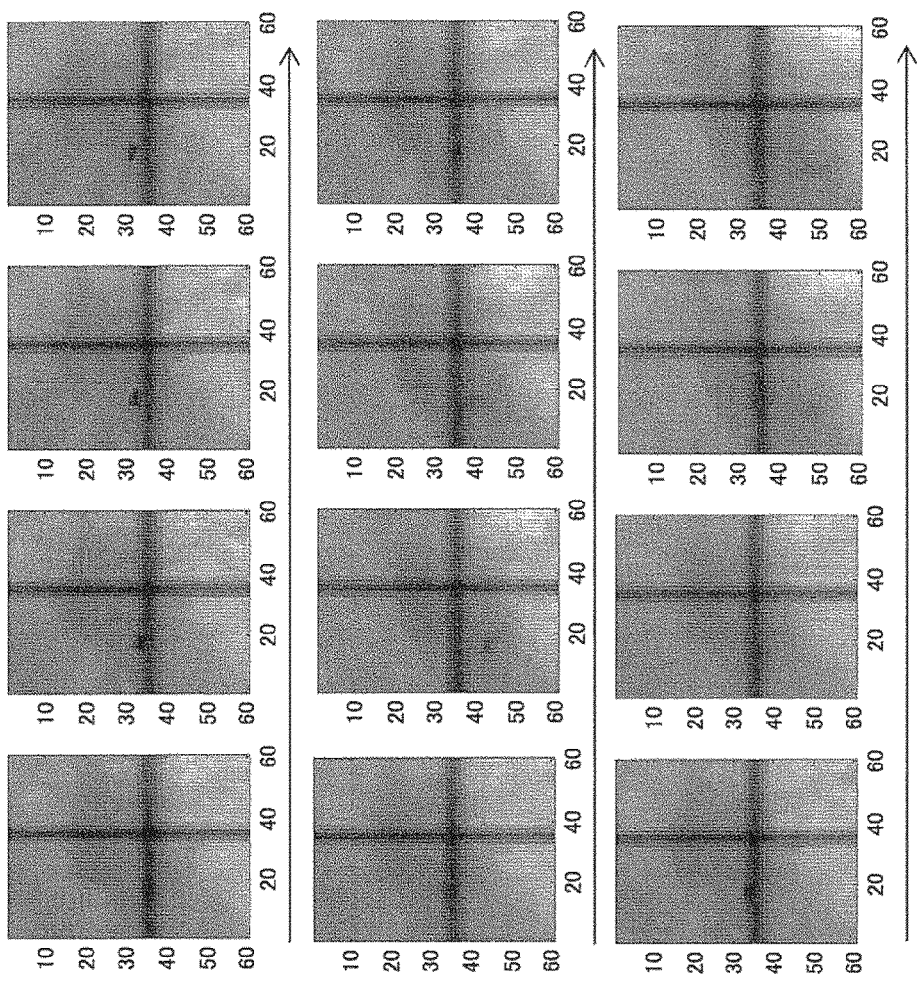
FIG. 18 is a diagram illustrating examples of transparent images of case data.

Next, an experiment result of using actual case data will be described. FIG. 18 is a diagram illustrating an example of transparent images before target portions and background portions with an ROI size of 60×60 are separated. In the example illustrated in FIG. 18, the transparent images continuous from the 1$^{st}$ to 12$^{th}$ frames are arranged in the time-series order from the left upper side to the right lower side.

Figure 19:
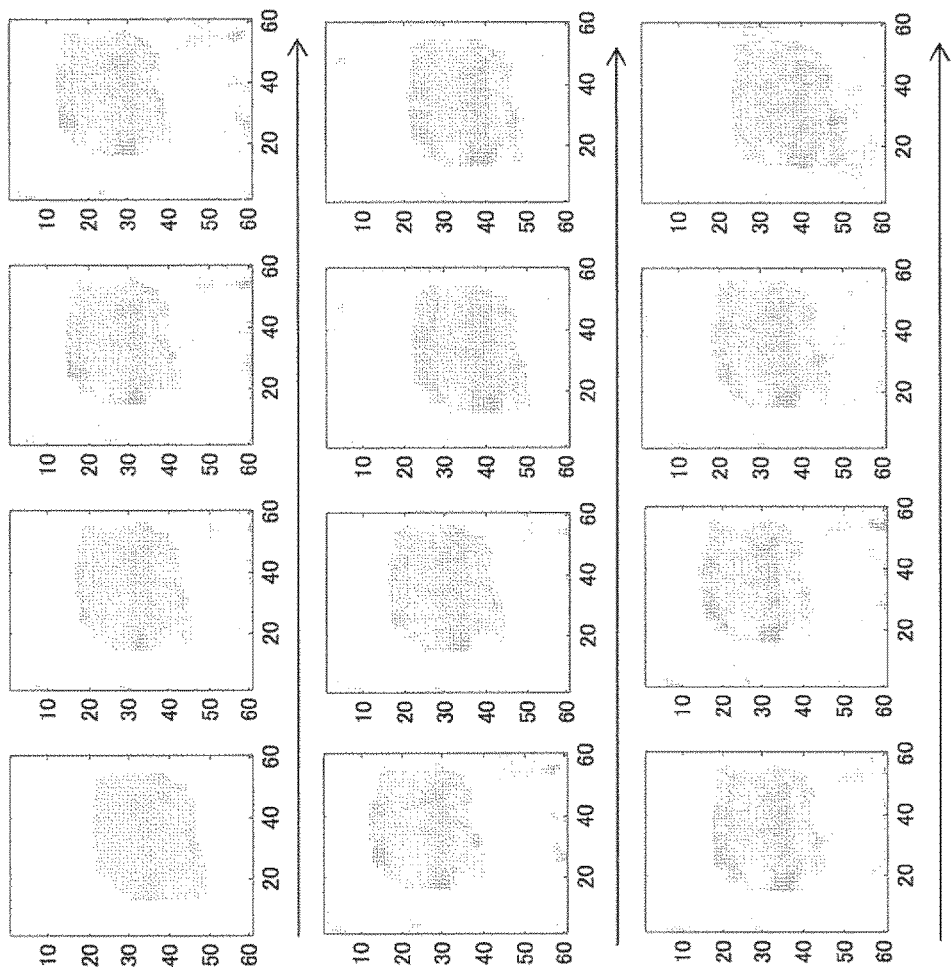
FIG. 19 is a diagram illustrating target portions separated from the transparent images illustrated in FIG. 18.
Figure 20:
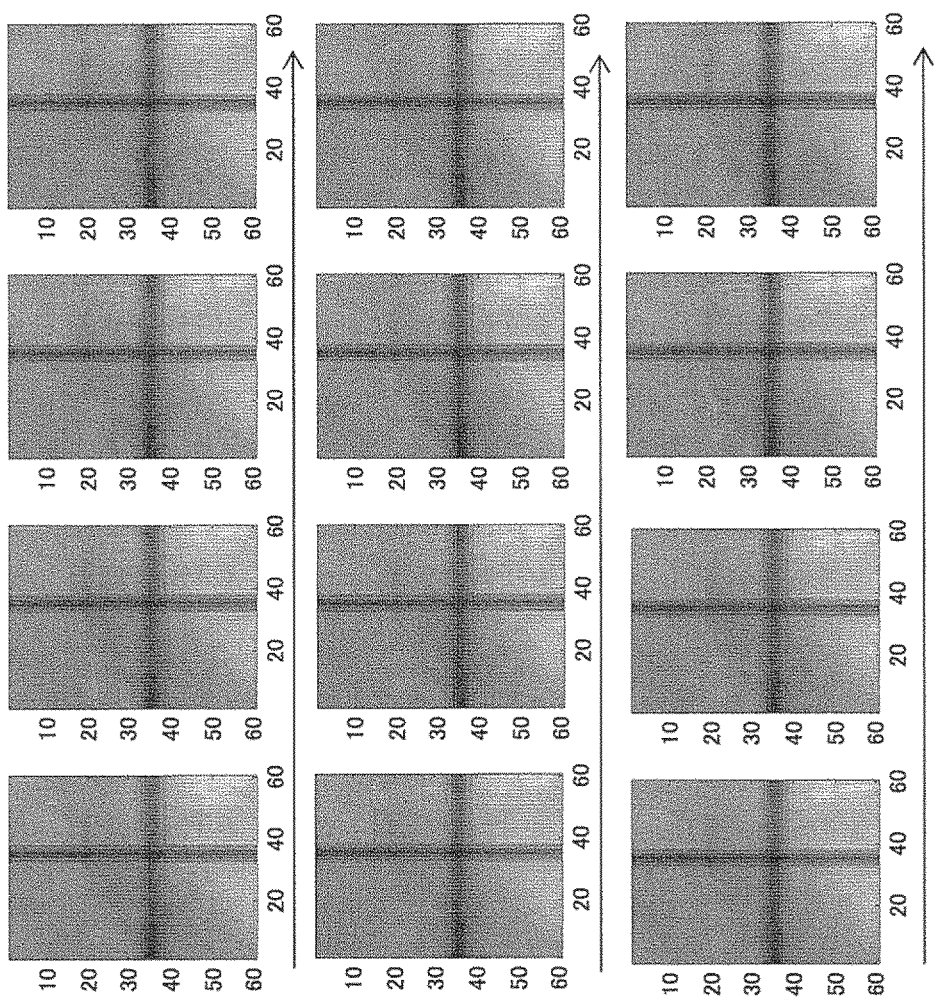
FIG. 20 is a diagram illustrating background portions separated from the transparent images illustrated in FIG. 18.

When the signal-processing method of this example is applied to each frame illustrated in FIG. 18, as illustrated in FIGS. 19 and 20, the target portion and the background portion can be separated.

Here, when the position of the separated target portion illustrated in FIG. 19 is measured using the TM method as an example of the position estimating method, the estimation error is 0.61±0.18 [mm]. Further, the shape and size of the target portion can be measured with high accuracy. The phantom data is updated by 100 frames, but the case data has a restriction that only 12 frames are used. Therefore, compared to the phantom data, the accuracy is slightly low. However, clinically sufficient high accurate measurement can be achieved. In the actual clinic, data of about 100 frames can be acquired by performing measurement for about 1 or 2 minutes before therapeutic irradiation. Therefore, high accurate separation and position measurement can be performed even on the case data.

On the other hand, when the position of the target portion is measured on the transparent images illustrated in FIG. 18 without separation of the target portion and the background portion using the TM method as an example of the position estimating method, the estimation error is 0.81±0.04 [mm]. Since the accuracy is improved more than in the BM method, the advantage of the TM method can be confirmed. However, in the TM method of this case, when contrast is high, for example, the contour of the target portion is clear, as in the BM method, high accuracy can be expected. Therefore, the contour portion with high contrast is set manually and visually as a point of interest by trial and error, and an ROI size in which the estimation error is the smallest is utilized. Since the visual and manual setting is a troublesome work in which full attention is necessary, the visual and manual setting in a busy clinical field may lay a burden on a setter. Accordingly, it is difficult to perform the high accurate measurement without separation of the target and the background.

As described above, according to the signal-processing method of this example, by separating the target portions and the background portions from the transparent images and estimating the position of the separated target portion, the position, shape, size, and the like of the target portion can be measured (estimated) with high accuracy from the transparent images acquired at different times.

Further, according to the signal-processing method of this example, it is possible to measure (estimate) the position, shape, size, and the like of the target portion with high accuracy, with safeness, and with low burden without insertion of a metallic marker as a measurement target.

(1.8) Modified Examples

In this example, as illustrated in the circled numeral 1 in FIG. 21, an example of a signal-processing method will be described when at least a part of a target portion is moved out of an ROI set in a transparent image.

For example, in the example illustrated in FIG. 11, parts of the target portion located at the positions "(m, n)=(2, 2) and (3, 2)" at the time t are moved to the positions (m, n)=(2, 1) and (3, 1) at the time (t+1).

In this case, the coefficient of each component of the variable vector I corresponding to other portions of the ROI (the positions (m, n)=(2, 3) and (3, 3) in the transparent image at the time (t+1) in the example illustrated in FIG. 11) is 0 in the transparent image at the time (t+1) (here, the variable forming the $I_a'$ is constant to formulate the above-described expression (f) as a simultaneous equation).

In the above-described example, when a value at the time t is expressed by a superscript, as in $I_{ij}(t)=I_{ij}^t$, the value is expressed as follows.

$$\hat{I}_{b23}=I_{23}^{t+1}, \hat{I}_{b33}=I_{33}^{t+1}$$

On the other hand, $$\hat{I}_{a24}+\hat{I}_{b23}=I_{23}^{t+1}, \hat{I}_{a34}+\hat{I}_{b33}=I_{33}^{t+1}$$

In the value above, inconsistency occurs.

Figure 21:
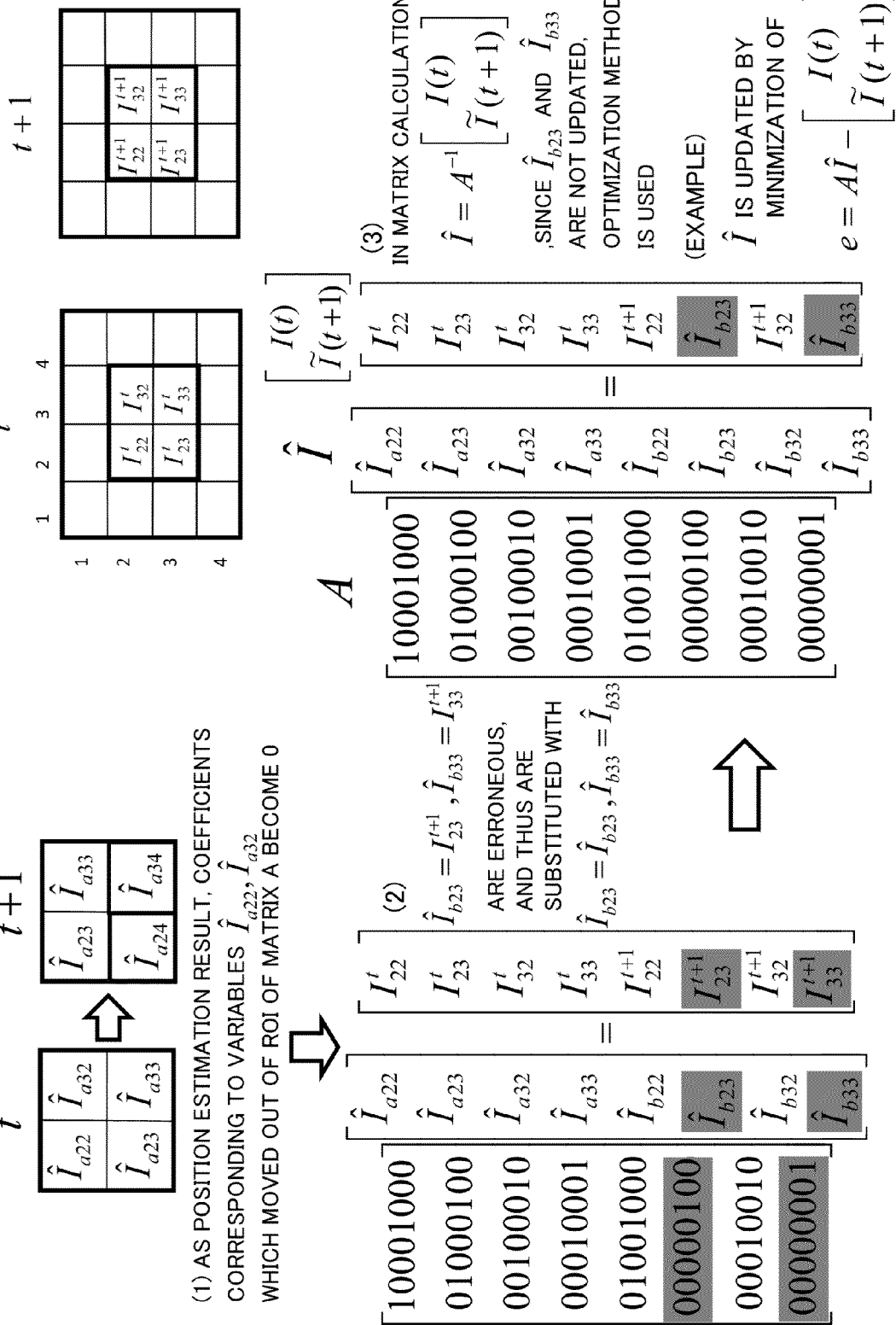
FIG. 21 is a diagram illustrating an example of a signal-processing method according to a modification example.

In this example, for example, the inconsistency can be avoided, $$\hat{I}_{b23}=\tilde{I}_{b23}, \hat{I}_{b33}=\tilde{I}_{b33}$$

when the above value is used (see the circled numeral 2 in FIG. 21).

However, when the following matrix is calculated without change, $$\hat{I} = A^{-1}\begin{bmatrix} I(t) \\ \tilde{I}(t+1) \end{bmatrix}$$

due to an erroneous restraint condition, $$\hat{I}_{b23}=\tilde{I}_{b23}, \hat{I}_{b33}=\tilde{I}_{b33}$$

that is, due to the value, $$\hat{I}_{b23}, \hat{I}_{b33}$$

this value is not updated.

As a result, under the restraint condition, only other variables are calculated, $$\hat{I}_{b23}, \hat{I}_{b33}$$

when the above variable is not a true value, other variables are erroneous values.

Accordingly, to exclude the influence of the erroneous restraint condition, the above-described optimization method such as a steepest descent method can be used.

For example, I' can be calculated by defining the error e by the following expression (i) and applying the optimization method such as a steepest descent method to the error e (see the circled numeral 3 in FIG. 21).

[Expression 11]

$$e = A\tilde{I} - \begin{bmatrix} I(t) \\ \tilde{I}(t+1) \end{bmatrix} \quad \text{(i)}$$

Thus, even when a part of the target portion is moved out of the ROI, the density distribution of the target portion can be calculated with higher accuracy. As a result, even in this case, the position, shape, size, and the like of the target portion can be measured (estimated) with higher accuracy.

(1.9) Others

A radiotherapy apparatus irradiating a target portion can be realized using information regarding the position of the target portion estimated by the above-described signal-processing unit 2 with a radiation ray.

Figure 22:
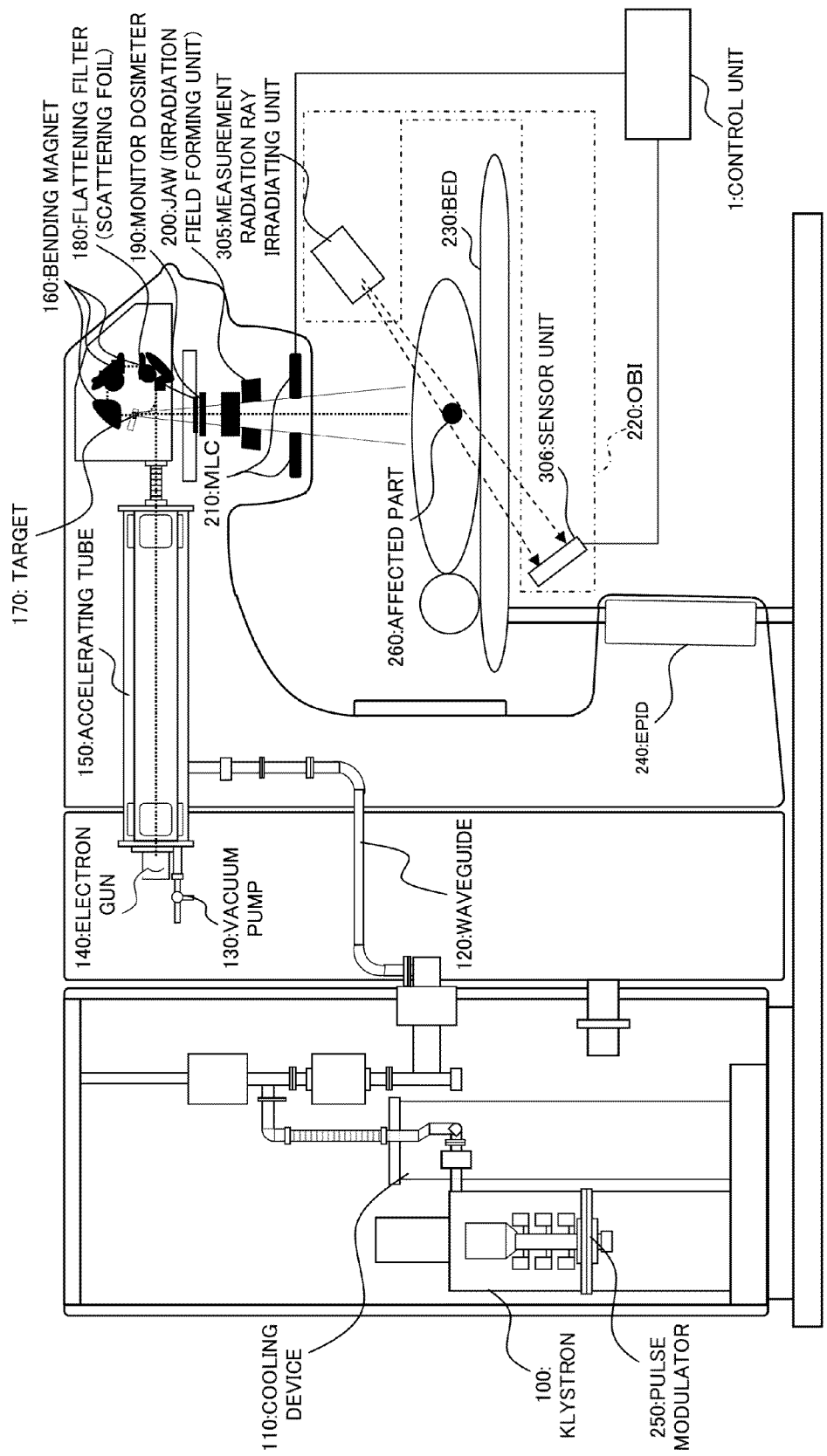
FIG. 22 is a diagram illustrating an example of a radiotherapy apparatus.

For example, as the radiotherapy apparatus illustrated in FIG. 22, a radiotherapy apparatus can be considered which includes a radiation ray generating unit (a pulse modulator 250, a klystron 100, a cooling device 110, a waveguide 120, a vacuum pump 130, an electron gun 140, an accelerating tube 150, a bending magnet 160, and a target 170) that generates a radiation ray irradiating an affected part 260 of a patient as the target portion; a collimator unit (an MLC 210) that forms an irradiation range of the radiation ray generated from the radiation ray generating unit in a desired shape; a signal-processing device (signal-processing unit 2) that estimates a temporal position variation of the affected part; and a driving control unit (a control unit 1) that calculates an irradiation position and the irradiation range of the radiation ray using information regarding the position of the affected part estimated by the signal-processing device and controls driving of the collimator unit based on the calculation result.

Thus, in radiotherapy, the affected part can be irradiated continuously and exactly with the radiation ray.

Further, a function serving as the above-described signal-processing unit 2 may be realized, when a computer (including a CPU, an information processing device, and various terminals) executes a predetermined application program (signal-processing program).

That is, the above-described program is an example of a signal-processing program causing a computer to realize an estimation function in a signal-processing device that estimates a temporal position variation of the target portion in transparent images expressed by transparent superposition of a target portion and a background portion different from the target portion. The signal-processing program includes a transparent image acquisition function of acquiring the transparent image in regard to the target portion at a given time t; a measurement vector generation function of taking an interest in a region of M×N pixels (pixels digitized in an analog image) or given regions with a given representative value of the plurality of pixel in the transparent images acquired by the transparent image acquisition function and generating a measurement vector b (t, $t_1, t_2, \ldots,$ and $t_K$) (where, K is a natural number) which corresponds to (K+1) times which consists of (K+1) MN luminance values in the region of interest of the K transparent images acquired at K times $t_1, t_2, \ldots,$ and $t_K$ prior to the time t; a variable vector updating function of updating variable vectors $I_{a1}, I_{a2}, \ldots,$ and $I_{aL}$ consisting of luminance values originating from the L target portions in the region of interest, respectively and a variable vector $I_b$ consisting of a luminance value of the background portion in the region of interest based on the measurement vector b, the background variable vector $I_b(t_p)$ and target variable vector $I_a(t_p)$ consisting of variable vectors $I_{a1}(t_p), I_{a2}(t_p), \ldots,$ and $I_{aL}(t_p)$ in regard to the region of interest of the transparent image at a time $t_p$ prior to the time t; and a variable vector calculating function of calculating a variable vector I including the variable vectors $I_a$ and $I_b$ updated by the variable vector updating function so that evaluation of an evaluation value PI defined by:

$$PI=f(A,I,b) \quad \text{[Expression 12]}$$

is calculated to an appropriate value such as an optimum value, where f is a deterministic or stochastic function, from the measurement vector b, the variable vector I, a coefficient matrix A of (K+1)MN×(L+1) MN regarding the positions of the L target portions and the background portion at the time t estimated using the variable vector I and the estimated positions of the L target portions and the background portion at the respective times being K previous times $t_1, t_2, \ldots,$ and $t_K$.

The acquisition of the transparent image by the transparent image acquisition function, the generation of the measurement vector b by the measurement vector generation function, the updating of the variable vector I by the variable vector updating function, and the calculation of the variable vector I by the variable vector calculating function are performed by shifting the time.

The program can be provided in the form of a non-transitory computer-readable recording medium, such as a flexible disc, a CD (a CD-ROM, a CD-R, a CD-RW, or the like), a DVD (a DVD-ROM, a DVD-RAM, a DVD-R, a DVD-RW, a DVD+R, a DVD+RW, or the like). In this case, a computer can read a signal-processing program from the recording medium, and transmit and store the signal-processing program in an internal storage device or an external storage device for use. Further, for example, the program may be recorded in a storage device (recording medium) such as a magnetic disk, an optical disc, a magneto-optical disc and may be provided from the storage device to a computer via a communication line.

Here, the computer means a concept including hardware and an OS (Operating System) and means hardware operating under the control of the OS. Further, when an OS is not necessary and hardware operates solely by an application program, the hardware itself corresponds to a computer. The hardware includes at least a microprocessor such as a CPU and a unit reading a computer program recorded in a recording medium.

An application program serving as the signal-processing program includes a program code causing the above-described computer to realize a function serving as the signal-processing unit 2 in the above-described computer. A part of the function may be realized by an OS rather than the application program.

As a recording medium according to this embodiment, not only the flexible disc, the CD, the DVD, the magnetic disk, the optical disc, and the magneto-optical disc described above can be used, but also various computer-readable media such as an IC card, a ROM cartridge, a magnetic tape, a punch card, an internal storage device (a memory such as a RAM or a ROM) of a computer, an external storage device or the like, a printing product or the like in which a sign such as a barcode is printed can be used.

The configurations and the processes of the radiotherapy apparatus and the signal-processing unit 2 described above may be selected or combined appropriately, as necessary.

For example, in the modified example, the position estimation method has been described when the target portion is moved out of the ROI. The method may be avoided by setting the range of the ROI to be sufficiently large and using dummy variables which are not actually estimated. However, when the dummy variables are used, a solution may not be calculated by inverse matrix calculation. A method of using an optimization method is used while correcting the erroneous restraint condition described in the modified example.

The signal-processing method of this example can be applied to, for example, estimation of the position, shape, size, and the like of a blood vessel photographed by an angiographic method, estimation of a variation in the position, shape, and size of each of a plurality of target objects in microscopic images when some or all of a plurality of microorganisms or the like with permeability overlap with each other and move, and non-destructive inspection.

Further, the position of the affected part 260 may be estimated using information regarding the position, shape, size, and the like of the target portion such as the affected part 260 estimated according to the signal-processing method of this example as input signals.

The invention claimed is:

1. A signal-processing device which processes transparent images each expressed by transparent superimposition of a target and a background different from the target, the device comprising:
    at least one processor configured to acquire the transparent images each including the target at a plurality of times, wherein:
    the at least one processor estimates a first component, which originates from the target, of the transparent image at a given time t among the plurality of times based on the transparent image at the given time t and an estimated value of a second component, which originates from the background, of the transparent image at the given time t, estimates a movement amount of the target based on the estimated first component, and updates the estimated first component and the estimated second component at the given time t based on the estimated movement amount and the acquired transparent images;
    a portion in each of the transparent images, at which portion the target is superimposed on the background, is a sum of the first component of the transparent image on the portion and the second component of the transparent image on the portion; and
    both of the first component and the second component in the portion comprise non-zero values for values representing the same image coordinates in an original image.

2. The signal-processing device according to claim 1, wherein the estimated first component and the estimated second component at the given time t are updated when shifting the time t to another time.

3. The signal-processing device according to claim 1, wherein the component includes luminance information indicating luminance intensities.

4. The signal-processing device according to claim 3, wherein the at least one processor:
    generates a measurement vector b indicating the luminance information in each transparent image at the time based on the transparent images at the plurality of times;
    sets or updates a target variable vector $I_a$ including the luminance information originating from the target of the transparent image at the time t and a background variable vector $I_b$ including the luminance information originating from the background of the transparent image at the time t;
    sets or updates a function A expressing position information in the transparent images of the target variable vector $I_a$ and background variable vector $I_b$ at the plurality of times;
    evaluates consistency among the measurement vector b, a variable vector I including the target variable vector $I_a$ and the background variable vector $I_b$, and the function A; and
    updates the function A or the variable vector I based on the evaluation result.

5. The signal-processing device according to claim 1, wherein the at least one processor:
    performs statistical analysis of the target and the background; and
    updates the estimated value based on the evaluation result and the statistical analysis result.

6. A signal-processing device which processes transparent images expressed by transparent superimposition of L (where, L is a natural number) targets and a background other than the targets, the device comprising:
    at least one processor configured to acquire the transparent image in regard to the targets at a given time t,
    wherein the at least one processor:
    generates a measurement vector b (t, $t_1$, $t_2$, . . . , and $t_K$) (where, K is a natural number) corresponding to (K+1) times which consists of (K+1)×M×N luminance values (where, M and N are natural numbers) in regions of interest of the (K+1) transparent images acquired at the time t and K times $t_1$, $t_2$, . . . , and $t_K$ prior to the time t, respectively, each of the regions of interest being a M×N region;
    updates variable vectors (hereinafter, referred to as target variable vectors $I_{a1}$, $I_2$, . . . , and $I_{aL}$) consisting of at least one luminance value originating from the L targets in the region of interest, respectively and a variable vector (hereinafter, referred to as a background variable vector $I_b$) consisting of at least one luminance value of the background in the region of interest based on the measurement vector b, the background variable vector $I_b(t_p)$ and target variable vector $I_a(t_p)$ consisting of L variable vectors $I_{a1}(t_p)$, $I_{a2}(t_p)$, . . . , and $I_{aL}(t_p)$ in regard to the region of interest of the transparent image at a time $t_p$ prior to the time t;

estimates a movement amount vector representing a movement amount of the targets based on the updated target variable vector $I_a$ estimates, based on the estimated movement amount vector, a coefficient matrix A of (K+1) MN ×(L+1) MN regarding the positions of the L targets and the background at the time t and the K times $t_1, t_2, \ldots$, and $t_K$, respectively; and calculates a variable vector I including the updated target variable vector $I_a$ and the updated background variable vector $I_b$ so that evaluation of an evaluation value PI defined by a function of the measurement vector b, the variable vector I, the estimated coefficient matrix A:

$$PI = f(A, I, b) \qquad \text{[Expression 1]}$$

is increased, where f is a deterministic or stochastic function, wherein the acquisition of the transparent image by the at least one processor, the generation of the measurement vector b by the at least one processor, the updating of the variable vector I by the at least one processor, and the calculation of the variable vector I by the at least one processor are performed by shifting the time, wherein a portion in each of the transparent images, at which portion the target is superimposed on the background, is a sum of a first component, which originates from the target, of the transparent image on the portion and a second component, which originates from the background, of the transparent image on the portion, and wherein both of the first component and the second component in the portion comprise non-zero values for values representing the same image coordinates in an original image.

7. The signal-processing device according to claim 6, wherein the at least one processor sets given initial values in the target variable vector $I_a$ and
sets, in the background variable vector $I_b$, a result obtained by subtracting the target variable vector $I_a$ in which the initial value is set from the measurement vector b.

8. The signal-processing device according to claim 6, wherein the at least one processor updates the variable vector I using the result calculated by the at least one processor.

9. The signal-processing device according to claim 8, wherein the at least one processor updates the background variable vector $I_b$ by the background variable vector $I_b$ calculated by the at least one processor, updates (L−1) variable vectors $I_{aj}$ by setting a result obtained by subtracting the updated background variable vector $I_b$ and the (L−1) variable vectors $I_{ai}$ (where, i=1, 2, . . . , and L, here, i ≠ j and j is a natural number that satisfies "0 <j <(L +1)") at a previous given time from the measurement vector b, and updates one non-updated variable vector $I_{aJ}$ by setting a result obtained by subtracting the updated background variable vector $I_b$ and the updated (L−1) variable vectors $I_{aj}$ (where, j=1, 2, . . . , and L, here, j ≠ J and J is a natural number that satisfies "0 <J <(L+1)") from the measurement vector b.

10. The signal-processing device according to claim 7, wherein the at least one processor estimates the coefficient matrix A based on the variable vector I set based on the initial value and the updated variable vector I.

11. The signal-processing device according to claim 7, wherein the at least one processor estimates the coefficient matrix A based on the variable vector I before the updating and the variable vector I after the updating.

12. The signal-processing device according to claim 10, wherein the at least one processor calculates the variable vector I using a gradient method.

13. The signal-processing device according to claim 11, wherein the at least one processor calculates the variable vector I using a gradient method.

14. The signal-processing device according to claim 6, further comprising:

the at least one processor configured to estimate temporal position variations of the targets based on the target variable vector $I_a$ in which an initial value is set by the at least one processor and the target variable vector $I_a$ updated by the at least one processor.

15. The signal-processing device according to claim 6, further comprising:

the at least one processor configured to estimate temporal position variations of the targets based on the target variable vector $I_a$ before the updating performed by the at least one processor and the target variable vector $I_a$ after the updating performed by the at least one processor.

16. A non-transitory computer-readable recording medium which records a program causing a computer, which processes transparent images each expressed by transparent superimposition of a target and a background different from the target, to realize:

a transparent image acquiring function of acquiring the transparent images each including the target at a plurality of times;

a first estimating function of estimating a first component, which originates from the target, of the transparent image at a given time t among the plurality of times based on the transparent image at the given time t and an estimated value of a second component, which originates from the background, of the transparent image at the given time t;

a second estimating function of estimating a movement amount of the target based on the estimated first component; and an updating function of updating the estimated first component and the estimated second component at the given time t based on the time t based on the estimated movement amount and the acquired transparent images, wherein a portion in each of the transparent images, at which portion the target is superimposed on the background, is a sum of the first component of the transparent image on the portion and the second component of the transparent image on the portion; and both of the first component and the second component in the portion comprise non-zero values for values representing the same image coordinates in an original image.

\* \* \* \* \*